US011319360B2

United States Patent
Koh et al.

(10) Patent No.: US 11,319,360 B2
(45) Date of Patent: May 3, 2022

(54) EXOSOME-BASED ANTICANCER AGENT

(71) Applicant: KOREA INSTITUTE OF SCIENCE AND TECHNOLOGY, Seoul (KR)

(72) Inventors: Eun-ee Koh, Seoul (KR); Eun Jung Lee, Seoul (KR); Yoo Soo Yang, Seoul (KR); In-San Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 181 days.

(21) Appl. No.: 16/475,052

(22) PCT Filed: Dec. 29, 2017

(86) PCT No.: PCT/KR2017/015784
§ 371 (c)(1),
(2) Date: Jun. 28, 2019

(87) PCT Pub. No.: WO2018/124835
PCT Pub. Date: Jul. 5, 2018

(65) Prior Publication Data
US 2020/0148746 A1   May 14, 2020

(30) Foreign Application Priority Data
Dec. 29, 2016 (KR) .................. 10-2016-0182573

(51) Int. Cl.
*C07K 14/71*  (2006.01)
*A61P 35/00*  (2006.01)
*C12N 9/12*   (2006.01)
*A61K 38/00*  (2006.01)

(52) U.S. Cl.
CPC .............. *C07K 14/71* (2013.01); *A61P 35/00* (2018.01); *C12N 9/12* (2013.01); *C12Y 207/10001* (2013.01); *A61K 38/00* (2013.01); *C07K 2319/03* (2013.01)

(58) Field of Classification Search
None
See application file for complete search history.

(56) References Cited

U.S. PATENT DOCUMENTS

2015/0329616 A1   11/2015  Uger et al.
2018/0104187 A1*  4/2018   Liu .................. G01N 33/57488

FOREIGN PATENT DOCUMENTS

WO   WO-2016/201323 A1   12/2016

OTHER PUBLICATIONS

Koh et al., "Exosome-SIRα, a CD47 Blockade Increases Cancer Cell Phagocytosis," Biomaterials, vol. 121, pp. 121-129 (Jan. 2017).
Tian et al., "A Doxorubicin Delivery Platform Using Engineered Natural Membrane Vesicle Exosomes for Targeted Tumor Therapy," Biomaterials, vol. 35, pp. 2383-2390 (2014).
Weiskopf et al., "Engineered SIRPα Variants as Immunotherapeutic Adjuvants to Anti-cancer Antibodies," Science, (Jul. 2013), vol. 341, No. 6141, pp. 1-13.
Johnsen et al., "A comprehensive overview of exosomes as drug delivery vehicles—Endogenous nanocarriers for targeted cancer therapy," Biochimica et Biophysica Acta 1846 (2014) 75-87 (available online Apr. 2014).

* cited by examiner

*Primary Examiner* — Anand U Desai
(74) *Attorney, Agent, or Firm* — United One Law Group LLC; Kongsik Kim; Jhongwoo Peck

(57) ABSTRACT

The present invention provides a recombinant exosome and uses thereof. More particularly, the present invention provides a recombinant exosome wherein a phagocytosis promoting protein is presented on the surface thereof.

12 Claims, 14 Drawing Sheets

Specification includes a Sequence Listing.

A

Control

Control
-exosome

SIRPα
-exosome

B

Control

Control
-exosome

SIRPα
-exosome mSIRPα

EXOSOME-BASED ANTICANCER AGENT

CROSS-REFERENCE TO RELATED APPLICATION

This application is the U.S. National Stage of International Application No. PCT/KR2017/015784, filed Dec. 29, 2017, and claims priority to Korean Patent Application No. 10-2016-0182573 filed on Dec. 29, 2016 and all the benefits accruing therefrom under 35 U.S.C. § 119, the contents of which are incorporated by reference in their entirety.

TECHNICAL FIELD

The present invention relates to a novel anticancer agent, and more specifically, to a novel anticancer agent that increases the phagocytosis of cancer cells.

BACKGROUND

Tumors avoid immune surveillance by expressing activating and inhibiting ligands that interact with receptors existing on the surface of immune cells to survive and proliferate. This interaction between tumor and immune cells prevents the tumor from being killed by the immune system (Pardoll, D. M., *Nat. Rev. Cancer.* 12: 252-264, 2012). One of mechanisms of immunological escape of tumor is the overexpression of CD47 which allows tumors to avoid innate immune surveillance. When CD47 binds to signal-regulatory protein α (SIRPα) of innate immune cells such as macrophages, the innate immune cells activate "do not eat me" signaling which leads to the avoidance of phagocytosis of the tumor by themselves, suggesting strong evidence for the therapeutic targeting of the CD47-SIRPα interaction since abundant CD47 expression in various malignant tumor cells results in a lower survival rate in cancer patients. Since the N-terminus of SIRPα contains the immunoglobulin superfamily V-like domain that interacts with the N-terminus of CD47, several competitive antagonists have been developed to block the interaction. Human CD47 blocking monoclonal antibody (CD47 mAb) proved efficacy in a variety of preclinical tumor models and triggered T cell mediated immunogenic destruction of tumors (Tseng, D. et al., *Proc. Natl. Acad. Sci. USA* 110: 11103-11108, 2013). In addition, CD47-SIRPα interactions may exhibit antagonistic effects with recombinant SIRPα proteins or SIRPα-FC fusion proteins. However, since weak interactions between native CD47 and SIRPα may limit the usefulness of wild-type SIRPα proteins as therapeutic antagonists, high-affinity mutants of SIRPα were developed and antagonized CD47 in cancer cells successfully. However, SIRPα mutants only acted as adjuvants to tumor-specific antibodies, but did not stimulate phagocytosis and inhibition of tumor growth beyond expectations (Sockolosky, J. T. et al., *Proc. Natl. Acad. Sci. USA* 113: E2646-E2654, 2016). In this regard, US Patent Publication No. 2015-0376288 discloses a therapeutic method for treating a pathogen infection by administering an agent that reduces the binding of CD47 to SIRPα in an infected cell on a host phagocytic cell.

SUMMARY

However, in the case of the above-mentioned prior art, administration of an anti-CD47 agent for treatment of infectious diseases reduces binding of SIRPα, which is unsuitable as a therapeutic agent for chemotherapy.

Accordingly, the present invention has been made to solve the above-mentioned problems, and it is an object of the present invention to provide a novel exosome-based anticancer agent which is effective for chemotherapy for removing cancer cells by increasing phagocytosis of the cancer cell by macrophages and dendritic cells. However, these problems are exemplary and do not limit the scope of the present invention.

In an aspect of the present invention, there is provided a recombinant exosome in which a phagocytosis promoting protein is presented on the surface thereof.

In another aspect of the present invention, there is provided a pharmaceutical composition for anticancer therapy comprising a therapeutically effective amount of the recombinant exosome and a pharmaceutically acceptable carrier.

Effect of the Invention

According to one embodiment of the present invention as described above, the production of effective exosome-based anticancer agent whose phagocytic activity of macrophages and dendritic cells against cancer cells is improved can be accomplished. In particular, the recombinant exosome in which SIRP is present on the surface thereof according to an embodiment of the present invention can stimulated the anti-cancer immune response more effectively by blocking SIRP-CD47 interaction with only small amount of exosomes since the SIRP is clustered in the form of a lipid raft on the surface of the exosome so that has high binding activity to the CD47 protein which is also clustered in the form of a lipid raft on the cancer cell surface. However, the scope of the present invention is not limited by these effects.

DETAILED DESCRIPTION OF EMBODIMENTS

Definition of Terms

Figure 1:
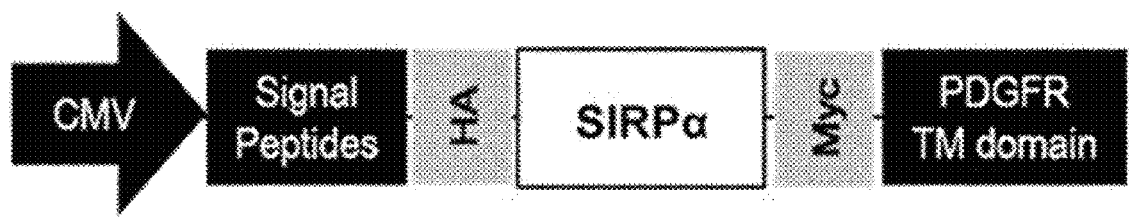
FIG. 1 is a schematic diagram representing the structure of a plasmid DNA expressing a SIRPα mutant (SIRPα-exosomes) according to an embodiment of the present invention.

As used herein, the term "exosome" refers to a small body of lipid bilayer secreted by cells in a living organism that perform specialized functions such as coagulation, intercellular signaling and cell waste management. Alternatively, the exosome may be referred to as "extracellular vesicle" or "cell-derived membrane vesicle". It is known to have specific nucleic acids and proteins therein and is releases into various body fluids.

As used herein, the term "SIRP (signal-regulatory protein)" refers to a regulatory membrane glycoprotein that is expressed predominantly in bone marrow cells and expressed in stem cells or neurons. Four kinds of SIRPs, i.e., SIRPα, SIRPβ, SIRPγ and SIRPδ are reported up to date. Among them SIRPα and SIRPγ are known to be inhibitory receptors and interact with the CD47 protein which is a transmembrane protein widely expressed in various cancer cells. The interaction between SIRP and CD47 is called the "don't eat me" signal. This interaction negatively regulates the effector function of innate immune cells, such as phagocytosis of tumor cells by them. This is similar to the self-signal provided by MHC I family molecules via Ig-like or Ly49 receptors. Cancer cells overexpressing CD47 activate SIRPα or SIRPγ to inhibit macrophage-mediated destruction. Recent studies have shown that high-affinity mutants of SIRPα increase the phagocytosis of cancer cells by masking CD47 on cancer cells (Weiskopf et al., *Science* 341 (6141): 88-91, 2013).

As used herein, the term "receptor tyrosine kinase (RTK)" refers to an important protein group that is involved in cell proliferation, differentiation, carcinogenesis, morphogenesis and the like, and the RTK includes, for example, epithelial growth factor receptor, nerve growth factor receptor, insulin receptor and hematopoietic stem cell proliferation factor receptor. The receptor activates the intracellular tyrosine kinase and transfer signals into the cell only when it binds extracellularly with these growth factors.

As used herein, the term "CD-47 binding domain" refers to a N-terminal domain that is capable of binding to CD47 and the N-terminal domain comprises up to 112 a.a.

DETAILED DESCRIPTION OF THE INVENTION

In an aspect of the present invention, there is provided a recombinant exosome in which a phagocytosis promoting protein is presented on the surface thereof.

According to the recombinant exosome, the phagocytosis promoting protein may be a fusion protein linked to the N-terminal of the transmembrane domain of the receptor tyrosine kinase, and the receptor tyrosine kinase may be a platelet-derived growth factor receptor (PDGFR), an epidermal growth factor receptor (FGFR), vascular endothelial growth factor receptor (VEGFR), hepatocyte growth factor receptor (HGFR), tropomyo sin receptor kinase (IRK), insulin receptor (IR), leukocyte receptor tyrosine kinase, angiopoietin receptor, receptor tyrosine kinase-like orphan receptors (DOR), discoidin domain receptor (DDR), rearranged during transfection receptor (RETR), tyrosine-protein kinase-like (PTK) to receptor tyrosine kinase, or MuSK (muscle-specific kinase).

Exosome is a kind of natural substance produced by cells, which is a biocompatible substance and can minimize the immune reaction. An "extracellular vesicle" or a "cell-derived membrane vesicle" included in the concept of exosome. Cell membrane protein expressed on the cell surface such as receptor can be presented on the surface by orienting it in the same direction as the cell. Thus, it is a substance that has a great advantage in presenting a cell surface protein on a surface thereof.

According to the recombinant exosome, the phagocytosis promoting protein may be SIRP or a fragment containing the CD47 binding domain of the SIRP, a Surfactant protein A, a Surfactant protein D or an anti-CD47 antibody, and the SIRP may be SIRPα, SIRPγ or high affinity variants thereof.

According to the recombinant exosome, the SIRP may comprise an amino acid sequence of any one of SEQ ID NOs: 1 to 61. According to the recombinant exosome may further include an anticancer agent. The anticancer agent may be an anti-cancer protein or an anti-cancer compound. In particular, the above-mentioned phagocytosis-promoting protein is preferably an anti-CD47 antibody or a SIRP protein which can block the signal transduction due to clustering of CD47 protein. In particular, the SIRP presented on the surface of the exosomes is clustering in the form of a lipid raft on the surface of the exosome due to the transmembrane domain of the platelet-derived growth factor receptor (PDGFR) and thus has high binding avidity to CD47 protein, which is also clustering in the form of lipid rafts on the surface of cancer cells, thereby blocks the SIRP-CD47 interaction with a small amount of exosomes, and stimulates the anti-cancer immune response more efficiently. The synergistic action of SIRPα loaded on the above exosome was first identified by the present inventors.

In the recombinant exosome, the anti-cancer protein may be an asparaginase, a protein toxin, an antibody specific for a cancer antigen, a fragment of the antibody, a tumor suppressor protein or an antiangiogenic factor. The protein toxin may be selected from the group consisting of Botulinum toxin, Tetanus toxin, Shiga toxin, Diphtheria toxin (DT), ricin, *Pseudomonas* exotoxin (PE), Cytolysin A (ClyA), and γ-Gelonin. The tumor suppressor protein is a protein that inhibits the development of tumors. Examples of the tumor suppressor protein include VHL (von Hippel Lindau), APC (Adenomatous polyposis coli), CD95 (cluster of differentiation 95), ST5 (Suppression of tumorigenicity 5), YPEL3 (Yippee like 3), ST7 (Supression of tumorigenicity 7), and ST14 (Suppression of tumorigenicity 14).

According the recombinant exosome, the anticancer compound is selected from the group consisting of methotrexate, pyrimidine analogs, hydroxyurea, purine analogs, alkylating agents, immunogenic cell death inducing agents, mitotic inhibitors, angiogenesis inhibitors, intercalating agents or radionuclides.

As the anticancer compound, the following compounds can be used:
(i) methotrexate;
(ii) pyrimidine analogs
5-fluorouracil, gemcitabine and arabinosylcytosine;
(iii) hydroxy urea;
(iv) purine analogs
mercaptopurine and thioguanine;
(v) alkylating agents
nitrogen mustard and cyclosporamide;
(vi) antibiotics
anthracycline, doxorubicin, daunorubicin, idarubicin and actinomycin D;
(vii) mitotic inhibitors
vincristine and taxol;
(viii) anti-angiogenesis agent
anti-VEGF antibody, combretastatin A4, Fumagillin, herbimycin A, 2-methoxyestradiol, OGT 2115, TNP 470, tranilast, XRP44X, thalidomide, endostatin, salmosin, angiostatin and kringle domains of plasminogen or apolipoprotein;
(ix) intercalating agents
carboplatin and cisplatin; and
(x) radionuclides
$^{18}$F, $^{90}$Y, $^{188}$Re, $^{32}$P, $^{89}$Sr, $^{165}$Dy, $^{186}$Re, $^{198}$Au, $^{153}$Sm, $^{131}$I, $^{169}$Er, $^{125}$I, $^{99}$Tc and $^{166}$Ho, etc.

According to the recombinant exosome, the immunogenic cell death inducer may be selected from the group consisting of an anthracycline-type anticancer agent, an anti-EGFR antibody, a BK channel agonist, bortezomib, a cardiac glycoside+non-immunogenic cell death inducer, cyclophosphamides, GADD34/PP1 inhibitor+mitomycin, LV-tSMAC, Measles viruse, and oxaliplatin. According to the recombinant exosome, the antracycline-type anticancer agent may be daunorubicin, doxorubicin, epirubicin, idarubicin, pixantrone, sabarubicin or valrubicin.

In another aspect of the present invention, there is provided a pharmaceutical composition for treating cancer in a subject comprising a therapeutically effective amount of the recombinant exosome and a pharmaceutically acceptable carrier.

According to the pharmaceutical composition, one or more anticancer agents may be further included. The composition containing a pharmaceutically acceptable carrier may be various oral or parenteral formulations, but it is preferably a formulation for parenteral administration. For the preparation of formulations, a diluent or excipient such as a filler, an extender, a binder, a humectant, a disintegrant, a surfactant, etc., may be used. Solid formulations for oral administration may include tablets, pills, powders, granules, capsules, etc., and these solid formulations may be prepared by adding at least one excipient, e.g., starch, calcium carbonate, sucrose or lactose, gelatin, etc. Additionally, lubricants, such as magnesium stearate, talc, etc., may be used, in addition to the simple excipient. Liquid formulations for oral administration may include suspensions, liquid medicines for internal use, emulsions, syrups, etc., and various excipients such as humectants, sweeteners, fragrances, and preservatives, may be used, in addition to the frequently-used simple diluents such as water and liquid paraffin. Formulations for parenteral administration may include sterile aqueous solutions, non-aqueous solvents, suspensions, emulsions, lyophilized formulations, suppositories, etc. Examples of the non-aqueous solvents and suspensions may include vegetable oils such as propylene glycol, polyethylene glycol, and olive oil; an injectable ester such as ethyl oleate; etc. Examples of the bases for suppositories may include Witepsol, macrogol, Tween 61, cacao butter, laurinum, glycerogelatin, etc.

The pharmaceutical composition may have one formulation selected from the group consisting of tablets, pills, powders, granules, capsules, suspensions, solutions, emulsions, syrups, sterilized aqueous solutions, non-aqueous solutions, lyophilized formulations, and suppositories.

The pharmaceutical composition of the present disclosure may be administered orally or parenterally. When administered parenterally, the pharmaceutical composition may be administered via various routes, including intravenous injection, intranasal inhalation, intramuscular administration, intraperitoneal administration, transdermal absorption, etc.

The composition of the present disclosure may be administered in a therapeutically effective amount.

As used herein, the term "therapeutically effective amount" refers to an amount sufficient for the treatment of diseases at a reasonable benefit/risk ratio applicable to a medical treatment, and the level of the effective dose may be determined based on the factors including the kind of a subject, severity of illness, age, sex, drug activity, drug sensitivity, administration time, administration route and dissolution rate, length of treatment, factors including drug(s) to be used simultaneously in combination, and other factors well-known in the medical field. The pharmaceutical composition of the present disclosure may be administered in an amount of 0.1 mg/kg to 1 g/kg, and more preferably, 1 mg/kg to 500 mg/kg. Meanwhile, the administration dose may be appropriately adjusted according to the age, sex, and health conditions of a patient.

The composition of the present disclosure may be administered as an individual therapeutic agent, in combination with other therapeutic agents for diabetes or muscular disease, or sequentially or simultaneously with a conventional therapeutic agent(s), and may be administered once or multiple times. It is important to administer an amount to obtain the maximum effect with a minimum amount without adverse effects considering all of the factors described above, and these factors can easily be determined by one of ordinary skill in the art.

BEST MODE FOR CARRYING OUT THE INVENTION

Hereinafter, preferred embodiments of the present disclosure will be described in detail. However, the present disclosure is not limited to embodiments explained herein but may be specified in various aspects. Rather, the embodiments are provided to sufficiently transfer the concept of the present disclosure to a person skilled in the art to thorough and complete contents introduced herein.

Example 1: Plasma DNA Construction

According to one embodiment of the present invention, a plasmid DNA expressing SIRPα variant (SIRPα-exosomes) which blocks CD47 on the surface of tumor cells and increases phagocytosis thereof was constructed. Specifically, the SIRPα mutant gene was obtained through a gene synthesis service (Cosmo Genetech Co.) and the DNA sequence (SEQ ID NO: 62) encoding the SIRPα variant (SEQ ID NO: 1) was inserted into frame between N-terminal signal peptide of platelet-derived growth factor receptor (PDGFR) and the membrane anchor of pDisplay vector (FIG. 1).

Example 2: Isolation of exosome

According to one embodiment of the present invention, HEK293T cells ($6 \times 10^6$) were cultured in Dulbecco's modified Eagle's medium (DMEM, 4,500 mg/L glucose) supplemented with 10% FBS and 1% antibiotics and the cell culture was maintained at 37° C. and 5% $CO_2$, and insulin-transferrin-selenium (Gibco) was added at a concentration of 80-90% confluency in a 15-cm culture dish and replaced with a serum-free DMEM. After 2 hours from the culture medium replacement, the cells were transfected with plasmid DNA (20 μg) encoding SIRPα variants using a transfection reagent (Lipofectamine 3000, Invitrogen) according to the manufacturer's instructions. After 48 hours of transfection, the cell culture supernatant was obtained by differential centrifugation to separate the exosomes, and the detailed procedure was as follows:

First, in order to remove cell debris and other cellular components in the culture medium containing exosomes, centrifugation was sequentially performed at 300 xg for 10 minutes, 2,000 xg for 10 minutes, and 10,000 xg for 30 minutes, and the culture was filtered with a 0.22 m filter and an ultra-centrifugation was carried out at 36,900 rpm for 2 hours using a 70 Ti rotor (Beckman Instruments). The resulting recombinant exosomes (SIRPα-exosomes) were resuspended in PBS containing a protease inhibitor (Roche) and the protein concentration of the isolated exosome was measured using a BCA protein assay kit (Bio-Rad), respectively.

Example 3: Characterization of Recombinant Exosome

The quality and characteristics of the recombinant exosome (SIRPα-exosomes) prepared according to one embodiment of the present invention are determined by western blotting (WB), flow cytometry, dynamic light scattering (DLS) and transmission electron microscope (TEM).

First, for Western blot analysis, the ultra-centrifuged recombinant exosomal pellet was dissolved using RIPA buffer (Cell Signaling Technology) containing a protease inhibitor cocktail (Calbiochem), and equivalent amount of exosomal protein (10 μg) was analyzed by SDS-PAGE and transferred to nitrocellulose membranes. Then, anti-Myc antibody (1:3000, Abcam, ab9106) and anti-HA antibody (1:500, Santa Cruz, sc-805) were added to BLAD to detect SIRPα expression, (1:500, Santa Cruz, sc-99010), anti-Tsg101 antibody (1:500, Santa Cruz, sc-22774) and anti-CD63 antibody (1:500, Santa Cruz, sc-15363) was used as exosome markers. HRP-conjugated secondary antibody (1:4,000, Sigma-Aldrich) was then added to the membrane and visualized by chemiluminescence. In addition, the expression of SIRPα on the surface of exosomes was analyzed by flow cytometry. First, 10 μg of exosomes were inserted into 4 μl aldehyde/sulfate latex beads (Invitrogen) in a final volume of 1 ml PBS for 2 hours at room temperature, then washed twice with PBS supplemented with 0.5% BSA, and the SIRPα was stained by incubating with Alexa fluor 488-conjugated secondary antibody (1:800, Jackson ImmunoResearch) and anti-Myc antibody (1:400, Abcam, ab9106) for 1 hour at 4° C. Fluorescence signals were analyzed using Accuri™ C6 flow cytometry analyzer (BD biosciences) and FlowJo_V10 software (FlowJo).

In addition, the shape of the recombinant exosome was analyzed as follows: Firstly, the recombinant exosome was located on copper grids equipped with a carbon film (Electron microscopy science), and negatively stained with uranyl acetic acid solution. The presentation of SIRPα on surface of the exosome was confirmed by immunoelectron microscopy. Specifically, the surface SIRPα was captured using anti-Myc antibody (1:100, Abcam, ab9106) and gold-conjugated antibody (1:50, Aurion) and image was obtained using a transmission electron microscopy (Tecnai). Finally, the size distribution of the recombinant exosomes was analyzed by dynamic light scattering (DLS) using a Zetasizer Nano ZS (Malvern Instruments, Ltd., UK) and the exosome size was measured at 25° C. (Z-average) at a fixed angle of 173°.

Figure 2:
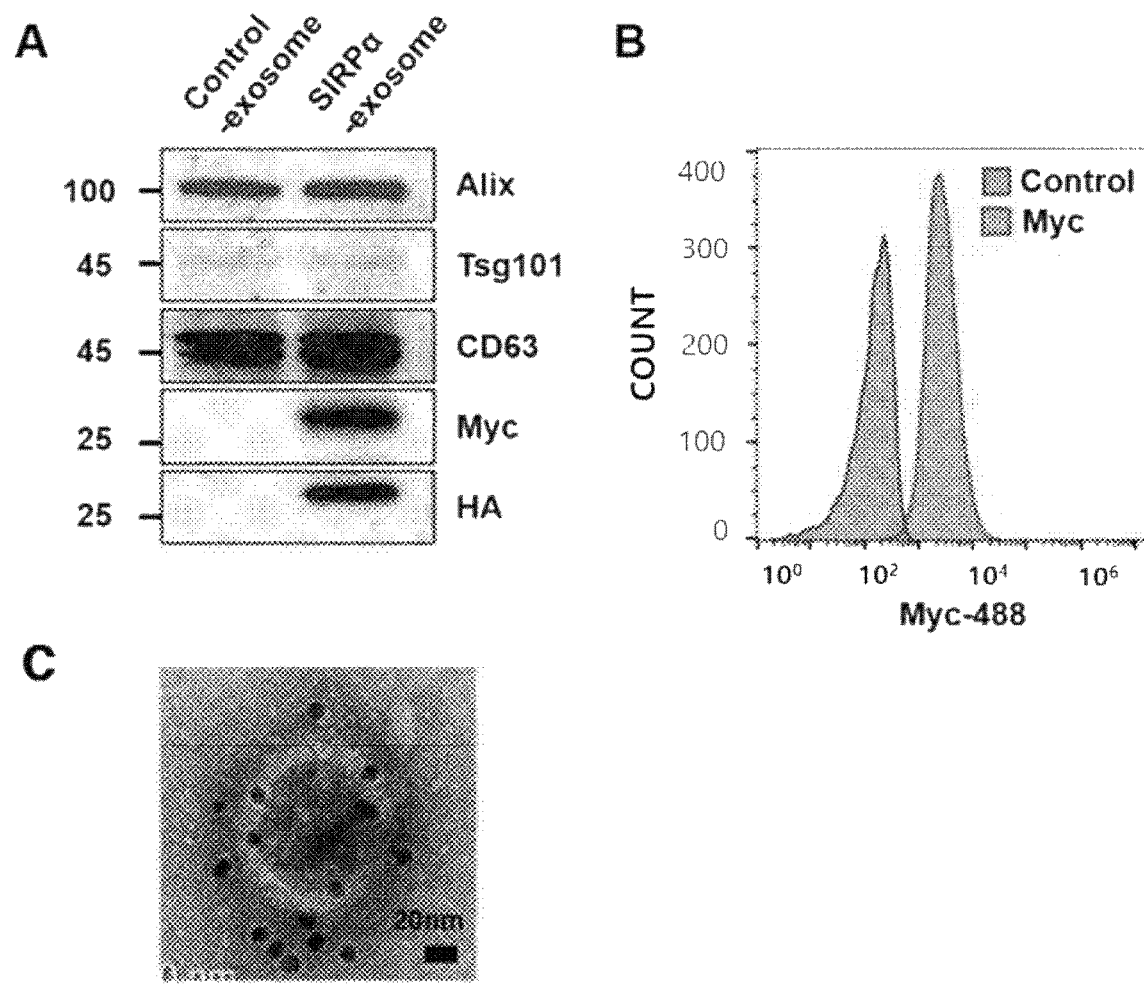
FIG. 2 shows a Western blot gel photograph showing the expression of recombinant exosome (SIRPα-exosomes) prepared according to an embodiment of the present invention (A); a histogram showing the expression of SIRPα on the exosome surface by flow cytometry (B); and an electron micrograph showing an image of SIRPα-exosome (C).
Figure 3:
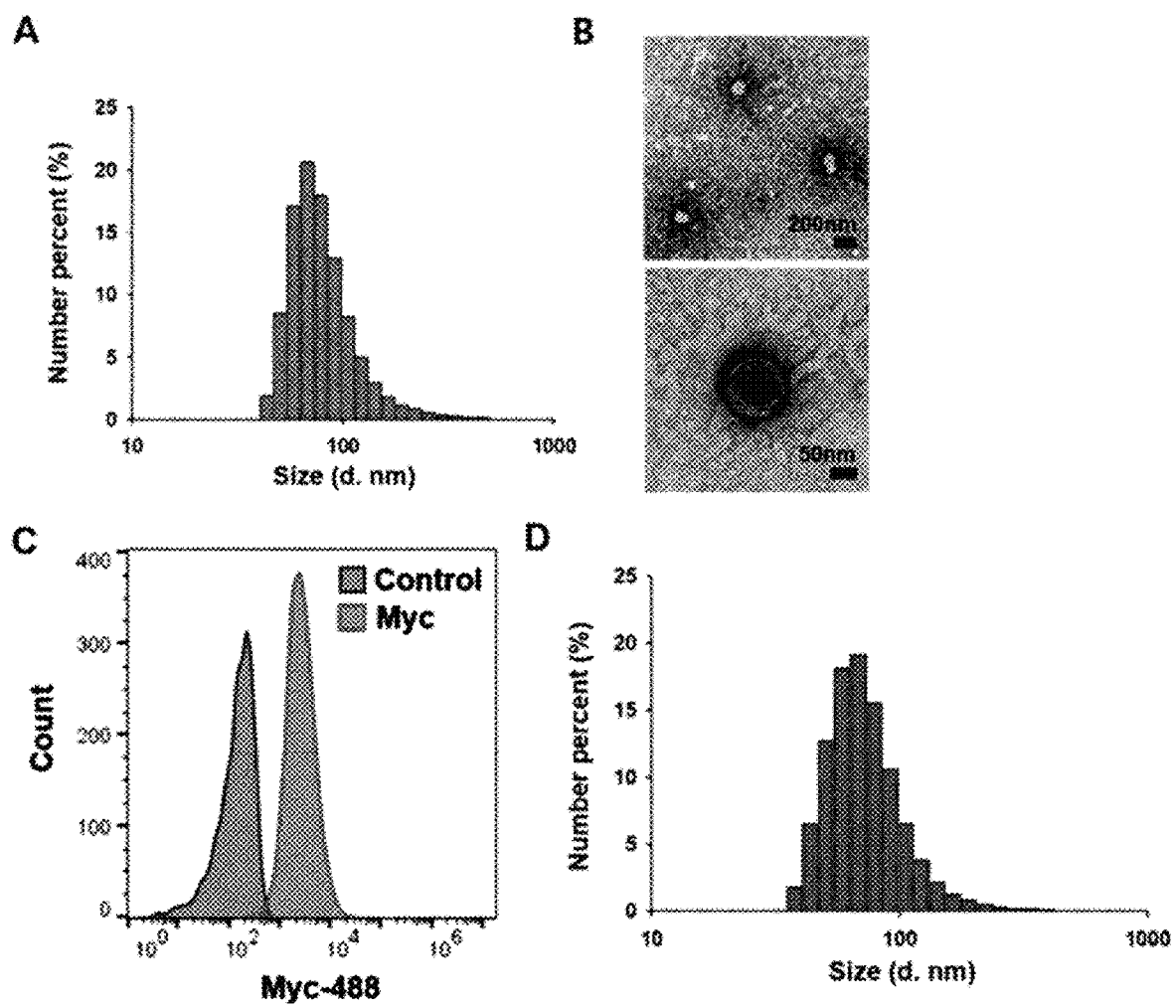
FIG. 3 shows a graph showing a dynamic light scattering (DLS) analysis of the size of SIRPα-exosomes prepared according to an embodiment of the present invention (A); a transmission electron microscope image of SIRPα-exosomes (B); a histogram representing the expression of SIRPα on the exosome surface by flow cytometry (C); and a graph representing a result of a dynamic light scattering (DLS) analysis of the size of control-exosomes (D).

As a result, it was observed that the purified SIRPα-exosome had a SIRPα variant on the membrane thereof and contained exosomal marker proteins (FIG. 2). Also, transmission electron microscope (TEM) images and dynamic light scattering (DLS) analysis confirmed that the average size of the recombinant exosomes was 100 nm with a round shape (FIG. 3).

Example 4: Expression and Purification of Monomeric SIRPα Protein

In order to obtain a monomeric SIPRα protein (mSIRPα) according to an embodiment of the present invention, a gene clone was obtained by PCR amplification using a primer encoding NH$_2$-Nde I-SIRPα variant-Myc-Hind III-COOH) and the gene clone was ligated with a pET-28a plasmid vector to express SIRPα with an N-terminal histidine tag.

Subsequently, the transformed bacterial cells were cultured in LB medium containing kanamycin at 37° C. until the OD$_{600}$ reached 0.5, and 0.5 mM isopropyl beta-D-1-thiogalactopyranoside (IPTG) (Bioneer, Korea) was added to induce protein expression. After incubation at 20° C. for 18 hours, the cells were centrifuged at 6,000 xg for 10 minutes, homogenized using an ultrasonic grinder, and the pellet was resuspended in lysis buffer (1 M Tris-HCl pH 8.0, 150 mM NaCl) and mSIRPα was purified through Ni-NTA affinity column chromatography, and anti-Myc antibody (1:5,000, Abcam, ab9106) and HRP-conjugated secondary antibody (1:4,000, Sigma Aldrich) were used for western blot analysis.

Figure 4:
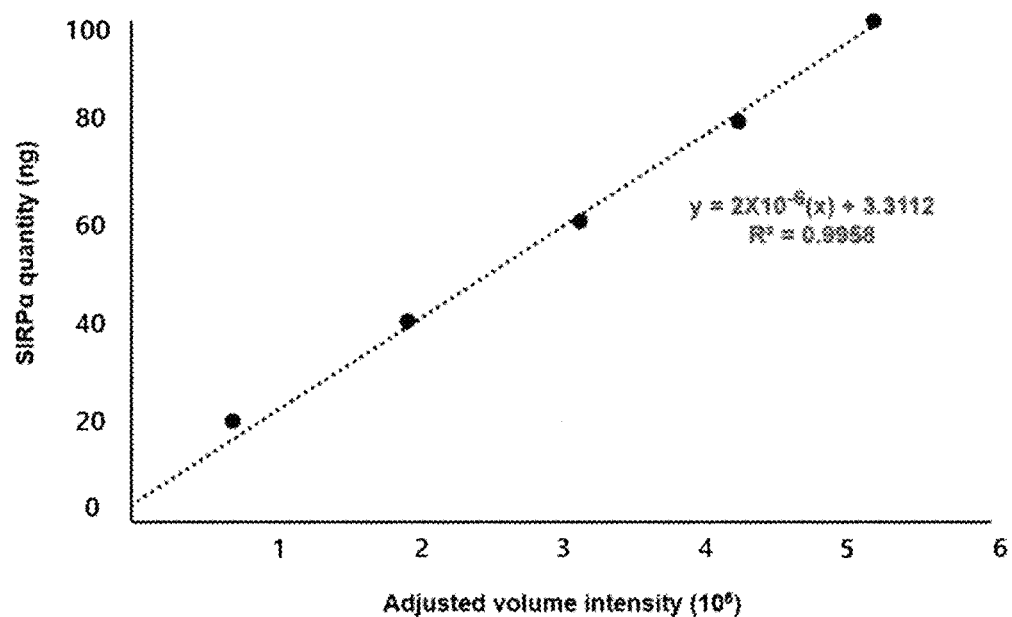
FIG. 4 shows a Western blot photograph showing the expression of purified recombinant SIRPα-Myc monomer protein (mSIRPα) according to an embodiment of the present invention (A); and a graph quantifying the amount of SIRPα of recombinant SIRPα-exosomes (B).

As a result, 100 µg of total protein and 2×10$^9$ SIRPα-exosomes were obtained from HEK293T cells, and the amount of SIRPα was quantified using a standard curve form the western blot image of the purified recombinant SIRPα-Myc monomer protein (mSIRPα). The quantified amount of SIRPα-exosome was less than 5 ng per 1 µg of exosomes (FIG. 4). The information on the primers used in the PCR amplification is summarized in the below table 1

TABLE 1

Primers for the PCR amplification

| Primer | Nucleotide sequence (5'→3') | SEQ ID NO |
|---|---|---|
| Forward | AAA CATATG GAA GAG GAG CTG CAG | 67 |
| Reverse | AAA AAGCTT TCA ATT CAG ATC CTC TTC | 68 |

Example 5: Cell Binding Assay

Cell binding analysis according to one embodiment of the present invention was carried out by culturing HT29 human colon adenocarcinoma (ATCC), Raji human B cell lymphoma (ATCC) and CT26.CL25 mouse colon cancer cells (ATCC) in RPMI-1640 culture medium supplemented with 10% FBS and 1% antibiotics and the cultures were maintained at 37° C. and 5% CO$_2$. HT29 and Raji cells were then cultured with the addition of an anti-human CD47 antibody (B6H12.2, Abcam, ab3283) and CT26.CL25 cells were incubated with anti-mouse CD47 antibody (Santa Cruz, sc-12731). For cell binding assays, HT29, Raji and CT26.CL25 cells (1×10$^6$) were incubated at 4° C. for 30 minutes with the addition of PBS, exosomes or mSIRPα, respectively. The cells were then incubated with anti-Myc antibodies (1:400, Abcam, ab9106) and detected by the addition of Alexa fluor 488-conjugated secondary antibody (1:800, Jackson ImmunoResearch). The cells were then measured using an Accuri™ C6 flow cytometer (BD Biosciences) and analyzed using FlowJo_V10 software (FlowJo). The binding specificity of SIRPα-exosomes to CD47 was analyzed by block experiments through pre-incubation of cells with anti-human CD47 antibody (1:100, Abcam, ab3283).

In addition, for fluorescence microscopy analysis, HT29 cells (2×10$^5$) were seeded in glass-bottom 4-well chambers and incubated with anti-Myc antibodies (1:400, Abcam, ab9106) and Alexa fluor 488-conjugated secondary antibody (1:800, Jackson ImmunoResearch). After removal of residual non-specific signals, the cells were fixed with Hoechst 33258 for 10 min at 25° C. for 10 min followed by fixing with 4% paraformaldehyde for 7 min after nuclear staining. The cell binding capacity of exosomes was examined by fluorescence microscopy (Nikon Eclipse Ti, Nikon) and analyzed using LAS AF Lite software (Leica).

Figure 5:
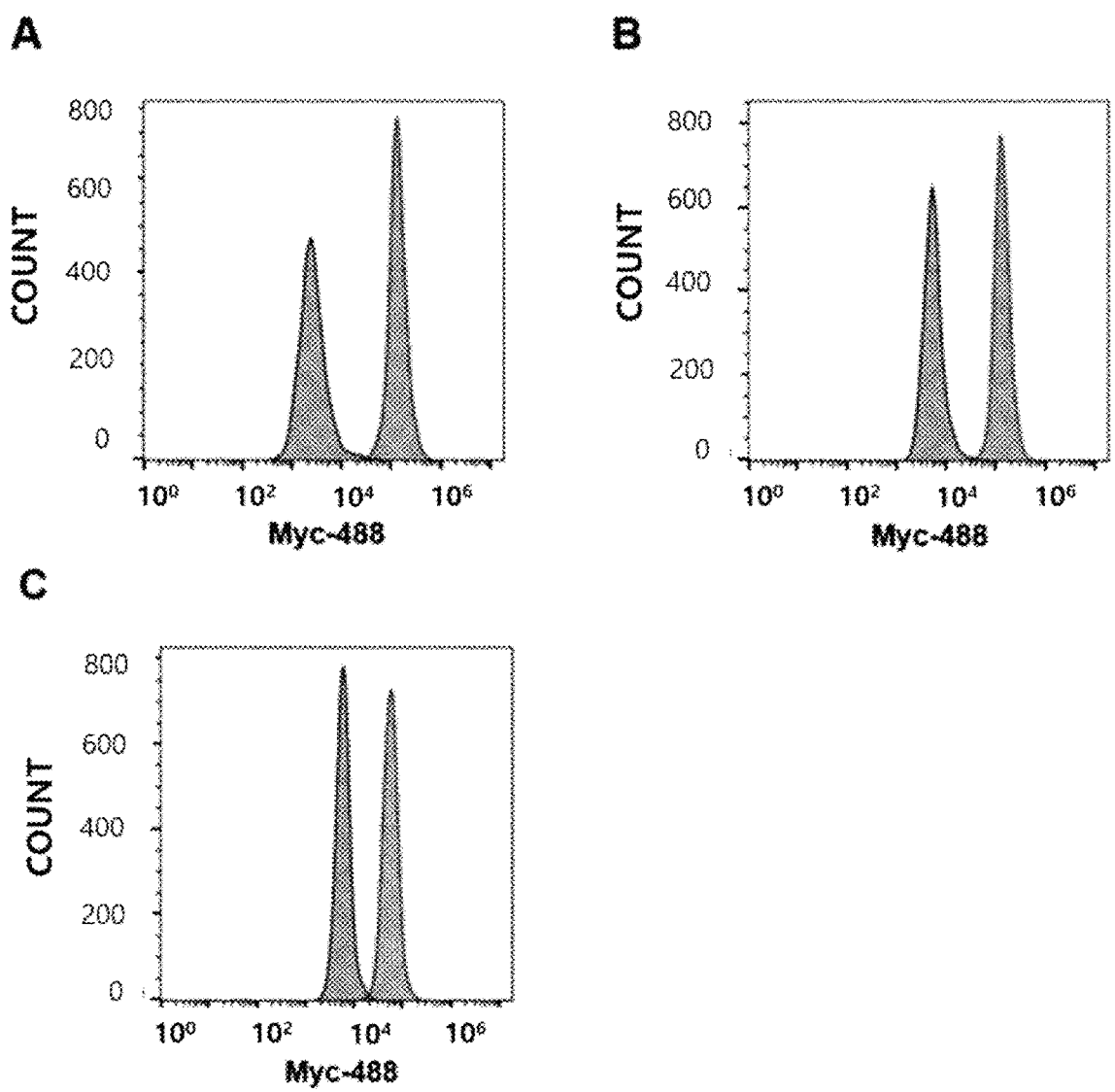
FIG. 5 is a series of graphs showing the expression of CD47 on the surfaces of HT29 (A), Raji (B) and CT26.CL25 cells (C), respectively, through cell binding assay according to an embodiment of the present invention.
Figure 6:
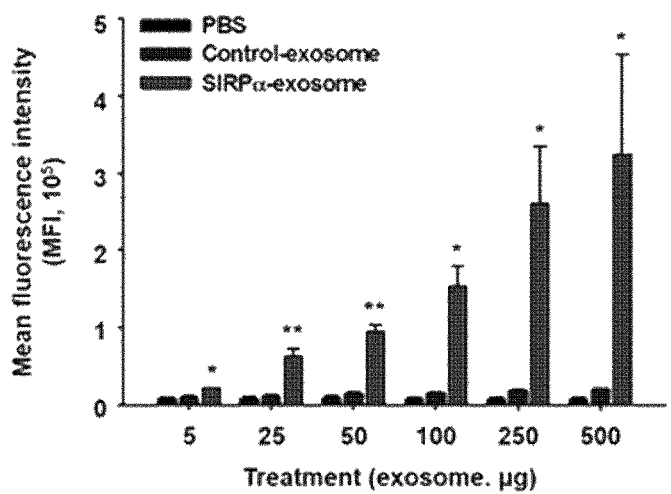
FIG. 6 shows a graph showing the fluorescence intensity of HT29 cells analyzed by CD47 binding activity of recombinant SIRPα according to an embodiment of the present invention (A); a histogram showing flow cytometry analysis (B); and a graph representing mean fluorescent intensity detected in Raji and CT26.CL25 cells, respectively (C).
Figure 6:
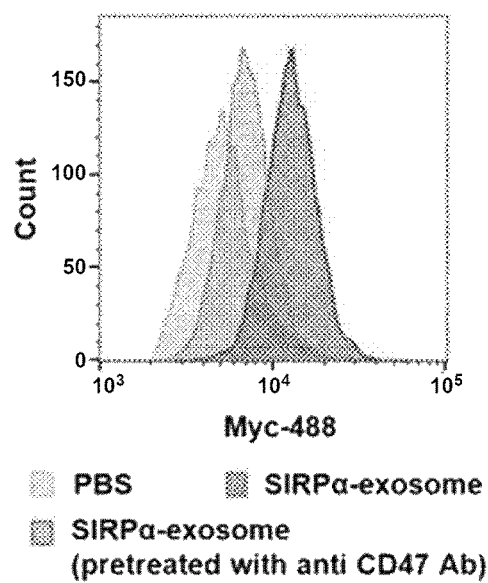
Figure 6:
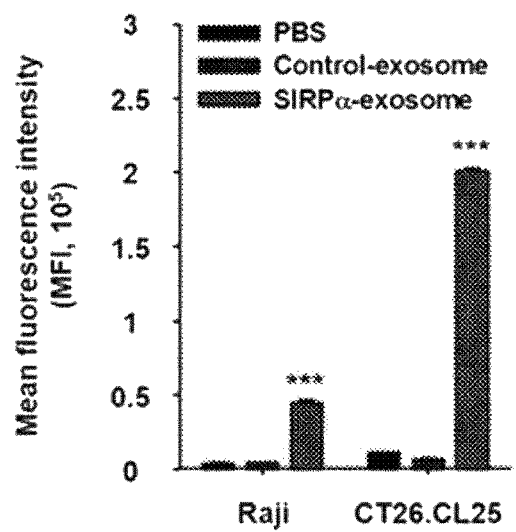
Figure 7:
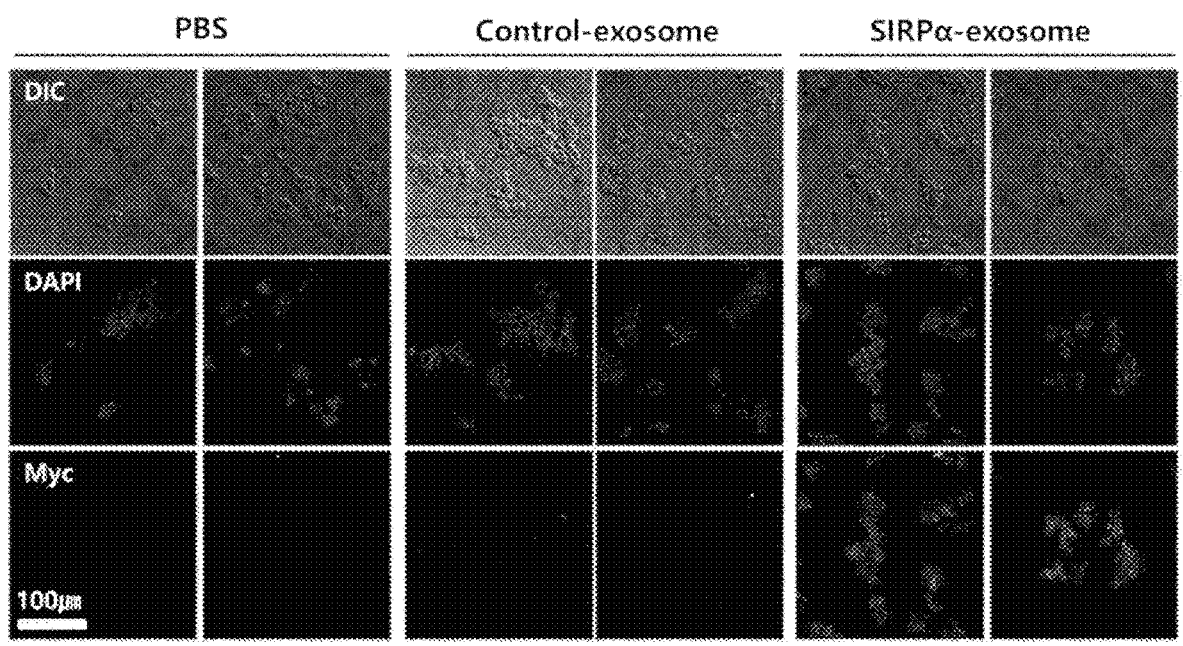
FIG. 7 is a series of fluorescence micrographs showing the effective binding of recombinant SIRPα in HT29 cells according to one embodiment of the present invention.

As a result, tumor cells were cultured with exosomes to confirm the ability of SIRPα-exosomes to antagonize cell surface CD47 in CD47$^+$ human tumor cell lines (FIG. 5). In addition, SIRPα-exosomes showed higher affinity for CD47 in the binding of HT29 tumor cell surface compared to the exosomes of the control group whose effect was dependent on the concentration of the SIRPα-exosome. The binding of SIRPα-exosomes was reduced by preincubation with anti-human CD47 antibody, indicating that SIRPα-exosomes specifically bind to CD47 on the tumor cell surface. As well, similar results were observed in human Raji Burkitt's lymphoma (Raji) and mouse CT26.CL25 colon cancer cells for binding of SIRPα-exosomes to CD47. These results indicate that the expression of membrane-associated SIRPα variants in exosomes has the ability to bind to CD47 in cancer cells (FIGS. 6 and 7).

Example 6: Analysis of Phagocytosis

According to one embodiment of the present invention, analysis of phagocytosis was performed to observe whether masking of CD47 with antagonistic activity of tumor cells increases phagocytosis of tumor cells. Specifically, BALB/c mice were sacrificed, and bone marrow cells were separated from leg bones to produce bone marrow-derived macrophages (BMDMs) for in vitro phagocytosis analysis. The isolated BMDMs were maintained in RPMI medium supplemented with 10% FBS and 1% antibiotic and were differentiated with macrophage colony-stimulating factor (M-CSF) for 7 days. The phagocytosis was analyzed by co-culture of BMDMs and cancer cells in serum-free RPMI medium for 4 hours. For flow cytometry, differentiated macrophages (2.5×10$^5$) were stained with 0.5 µM CellTracker™ Green and the exosomes or mSIRPα proteins were preincubated with cancer cells and BMDMs were then incubated with the mixture for 4 h. The rate of phagocytosis was assessed as a percentage of double positive signals using the Accuri™ C6 flow cytometry analyzer (BD biosciences) and FlowJo_V10 software (FlowJo).

For fluorescence microscopy analysis to measure the phagocytosis index (PI), BMDMs stained with CellTracker™ Green (Thermo fisher scientific) was inoculated on a 35 mm glass-bottom dish at a density of 2.5×10$^5$, and a mixture of HT29 cells (1×10$^6$) was stained with pHrodo Deep red (Thermo fisher scientific) and the exosomes were treated with macrophages. After 4 hours of co-culture, the engulfment of HT29 cells by macrophages was analyzed by fluorescence microscopy (Nikon Eclipse Ti, Nikon) as a red positive signal associated with phagocytic cell formation in macrophages.

Figure 8:
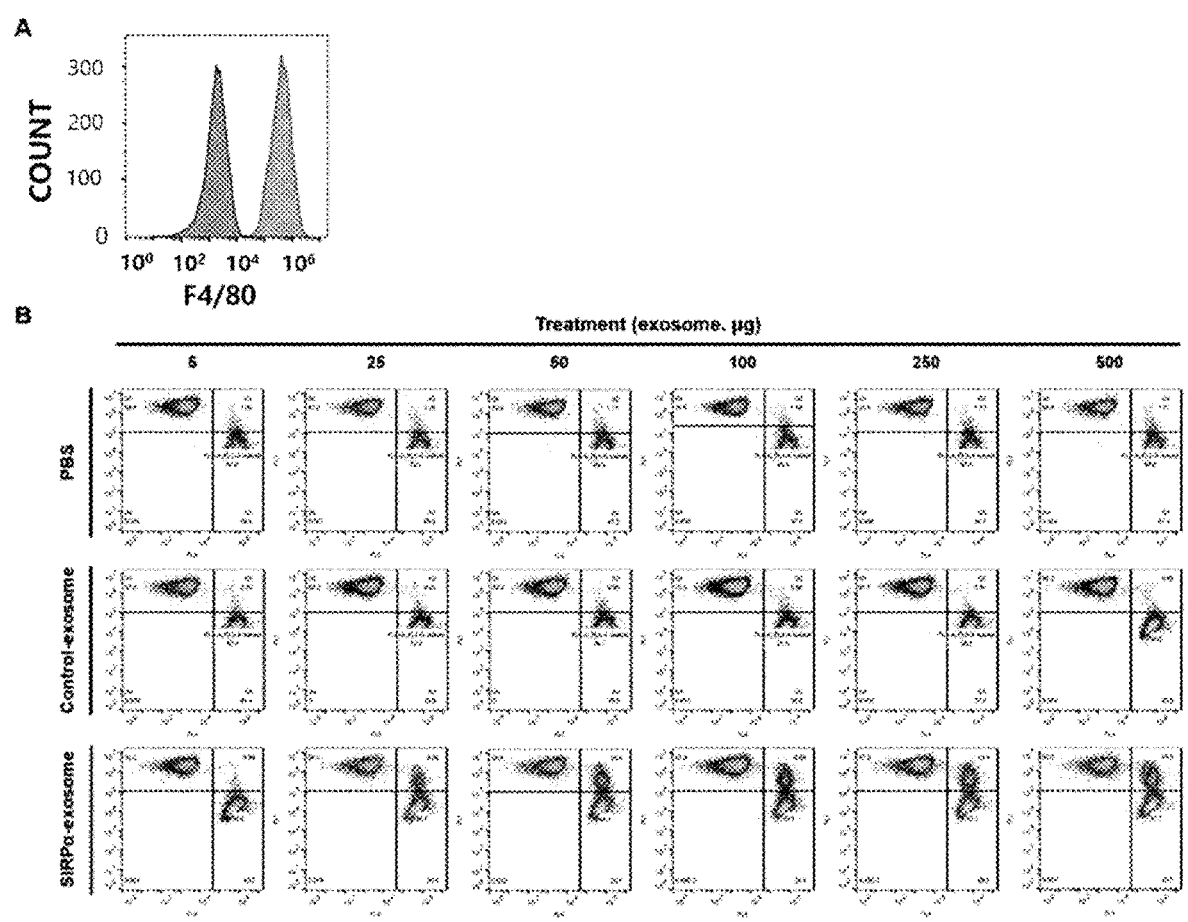
FIG. 8 shows a histogram representing a FACS analysis of the differentiation of bone marrow-derived macrophages (BMDMs) according to an embodiment of the present invention (A); and a series of histograms representing FACS data obtained by analyzing the phagocytosis of cells.
Figure 9:
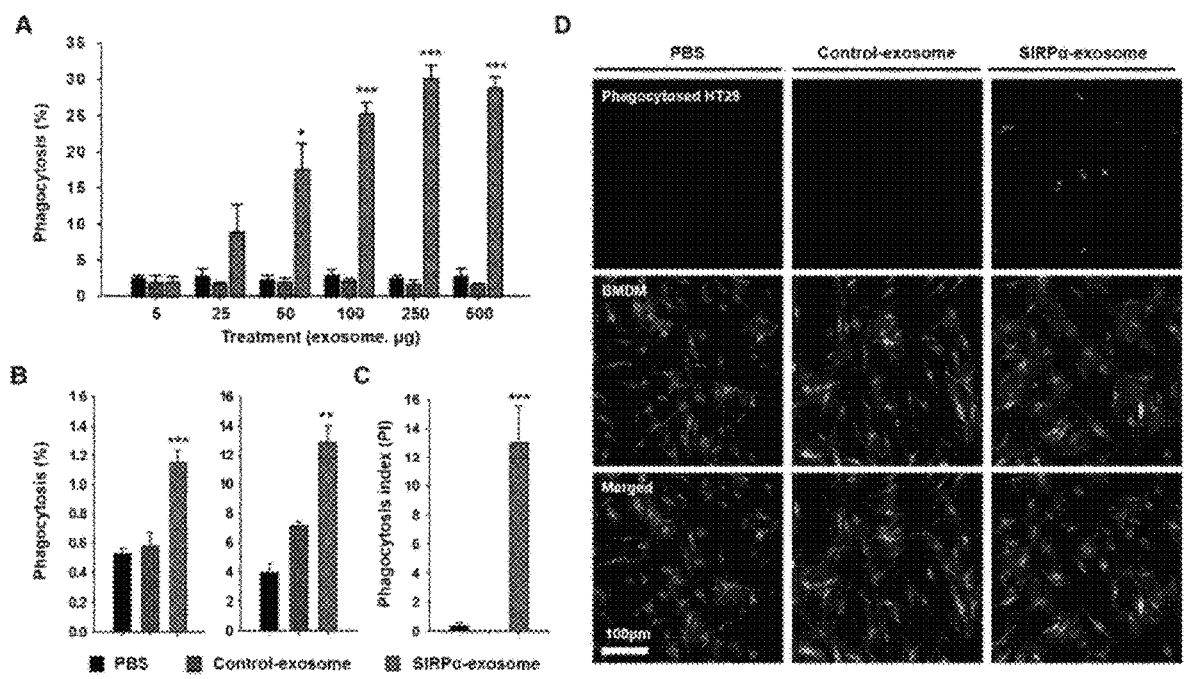
FIG. 9 shows a graph representing an increase in phagocytosis by SIRPα-exosomes according to an embodiment of the present invention (A); a graph representing analysis of phagocytosis of Raji and CT26.CL25 cells by bone marrow-derived macrophages (BMDMs) (B); a graph showing a phagocytosis index (PI) (C) and a series of fluorescence microscopic images representing the appearance of HT29 cells engulfed by bone marrow derived macrophages (BMDMs).

As a result, the phagocytosis by macrophages with double positive signals (deep red and green) was found to increase in a concentration-dependent manner in the SIRPα-exosome treated group compared to the control group (PBS-treated or control-exosome-treated) (FIG. 8) and the result was similar in Raji and CT26.CL25 colon cancer cells treated with SIRPα-exosomes. In addition, treatment of SIRPα-exosomes increased the phagocytosis of tumor cells, indicating that PI was significantly increased in the SIRPα-exosome treated group (FIG. 9). Thus, blocking the interaction of CD47-SIRPα with SIRPα-exosomes is associated with an increase in the phagocytosis of various cancer cells by bone marrow-derived macrophages (BMDMs).

Example 7: Study of In Vivo Distribution

To examine in vivo distribution of SIRPα-exosomes according to one embodiment of the present invention, exosomes were labeled with Cy5.5-NHS. After the treatment of Cy5.5-NHS dye (1 jag) to 100 jag of exosomes, the exosomes were incubated at room temperature for 2 hours and centrifuged for 45 minutes using an airfase centrifuge (Beckman coulter). The washed exosomal pellet was then resuspended in PBS after washing twice to remove unbound dye and the fluorescence intensity was measured using a fluorescence microplate reader (Infinite M200 Pro, TECAN) and normalized. In addition, Cy5.5-labeled exosomes (500 µg), free dyes and PBS were intravenously administered to HT29 tumor-bearing BALB/c nude mice respectively and the fluorescence intensity of all samples was normalized to the same value using the data obtained with fluorescence microplate reader. In vivo whole-body imaging of mice was performed at various time points (5 minutes, 2 hours, 4 hours, 8 hours, 16 hours and 24 hours) using IVIS imaging system (Caliper Life Sciences). In addition, to analyze the fluorescence intensity of the tumor, total photons per square centimeter per steradian in the ROI were calculated using Analysis Workstation software (Advanced Research Technologies Inc.) Mice were sacrificed at the time of injection and tumors and major organs including liver, lung, spleen, kidney, and heart were excised and analyzed in the same manner as above.

Figure 10:
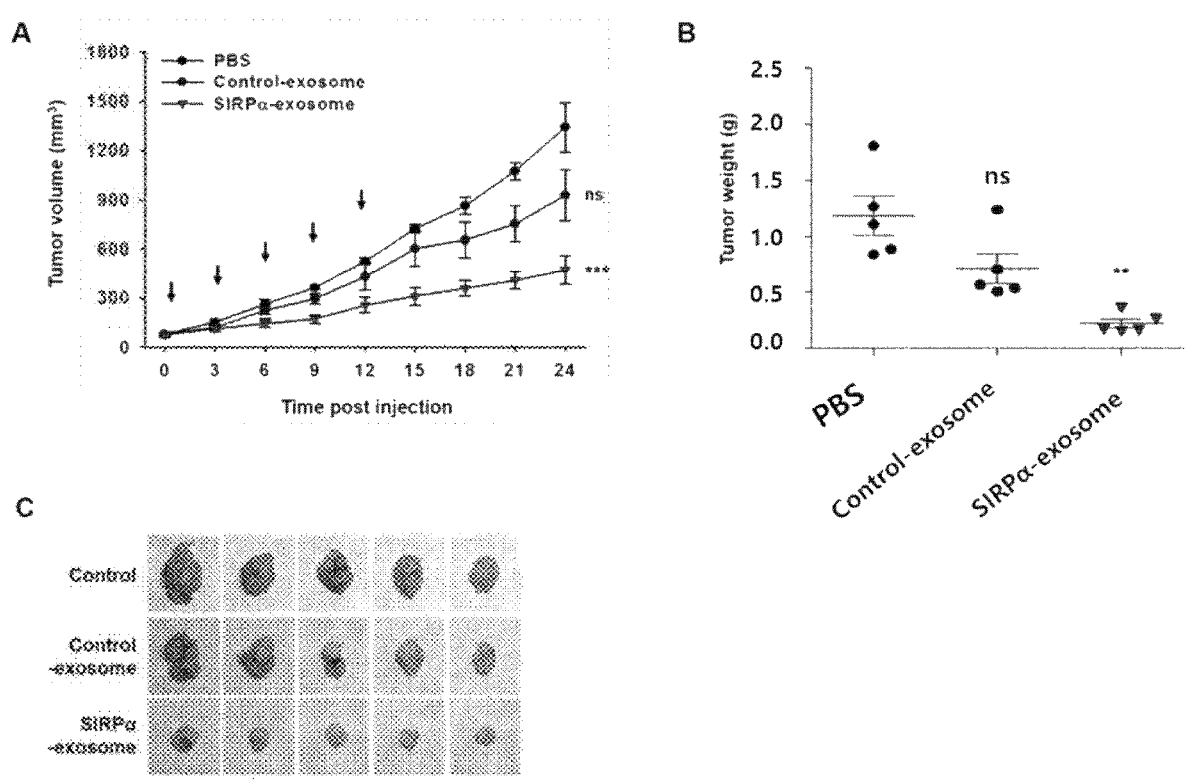
FIG. 10 shows a graph showing tumor growth in tumor-bearing immunodeficient mice administered with SIRPα-exosomes according to an embodiment of the present invention (A); a graph showing weight of excised tumors of the tumor-bearing immunodeficient mice (B) and a series of photographs showing the excised tumors (C).

As a result, the mean weight of the excised tumors was significantly lower in the SIRPα-exosome treated group than in the control group, consistent with the observed regression of tumor growth (FIG. 10).

Example 8: Anti-Tumor Effect Assay

Immuno-deficient BALB/c nude mice and immunocompetent BALB/c mice for in vivo experiments according to one embodiment of the present invention were used as xenograft tumor model animals at 7 weeks of age and were managed at the accommodation facilities of the Korea Institute of Science and Technology (KIST). Subsequently, HT29 cells ($1 \times 10^7$) were subcutaneously inoculated on the left leg of BALB/c nude mice and tumors were grown for one week and then injected with control-exosomes, SIRPα-exosomes and control PBS five times every 3 days, respectively. Then, for analysis of the local anti-tumor effect, 100 µg of exosomes were injected into the tumor of the mice. For the systemic effect of SIRPα-exosomes on tumor growth, exosomes (200 µg) and PBS were intravenously injected into HT29 tumor-bearing mice 5 times every 3 days via tail vein and the tumors were excised and weighted when the tumors were grown to 1000 mm³. In addition, CT26.CL25 cells ($1 \times 10^6$) were implanted subcutaneously in the left leg of immunocompetent BALB/c mice, and after one week, 200 µg of exosomes, 200 µg of SIRPα-exosomes, 1 µg of mSIRPα (corresponding to the amount of SIRPα in 200 µg of SIRPα-exosomes), or PBS was injected through the tail vein of each of the above mice (n=7 per each group, respectively) and the tumor was excised and weighted.

Figure 11:
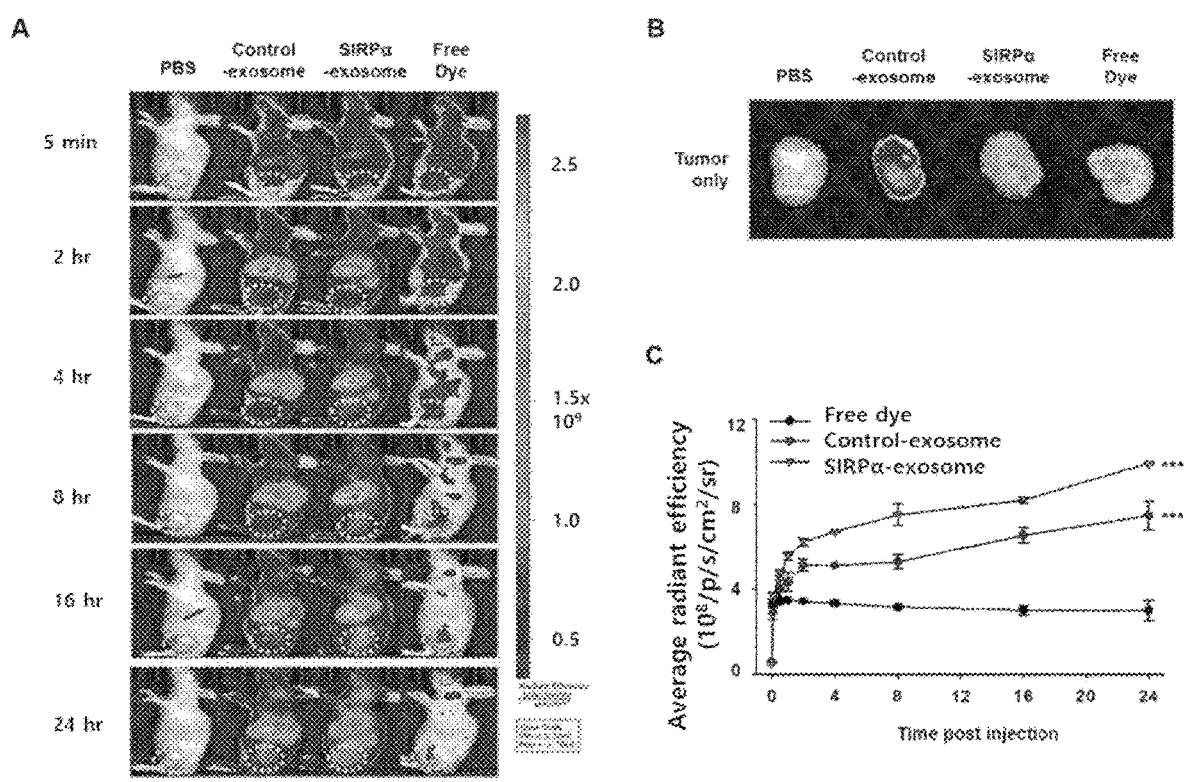
FIG. 11 represents an analysis of the antitumor effect of SIRPα-exosomes according to an embodiment of the present invention: (A) a series of photographs showing the biodistribution of Cy5.5-labeled exosomes in HT29 tumor-bearing mice; (B) a photograph showing excised tumors at 24 hours after injection of Cy5.5-labeled exosomes; and (C) a graph representing the change in the average radiation efficiency in the HT29 tumor-bearing mice.
Figure 12:
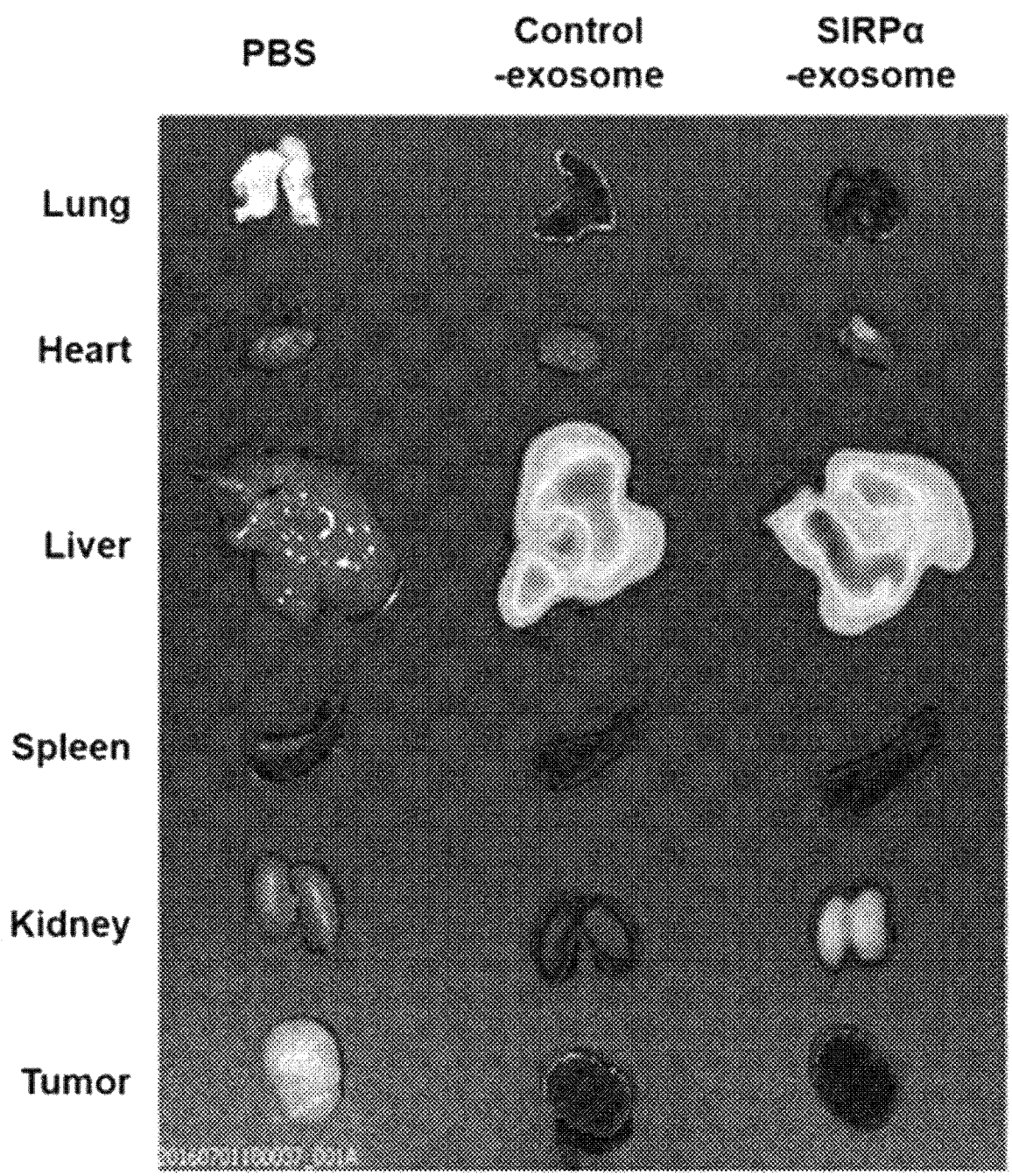
FIG. 12 is an IVIS image obtained by injecting Cy5.5-labeled exosomes according to an embodiment of the present invention into mice showing the results of detecting fluorescence in various organs.
Figure 13:
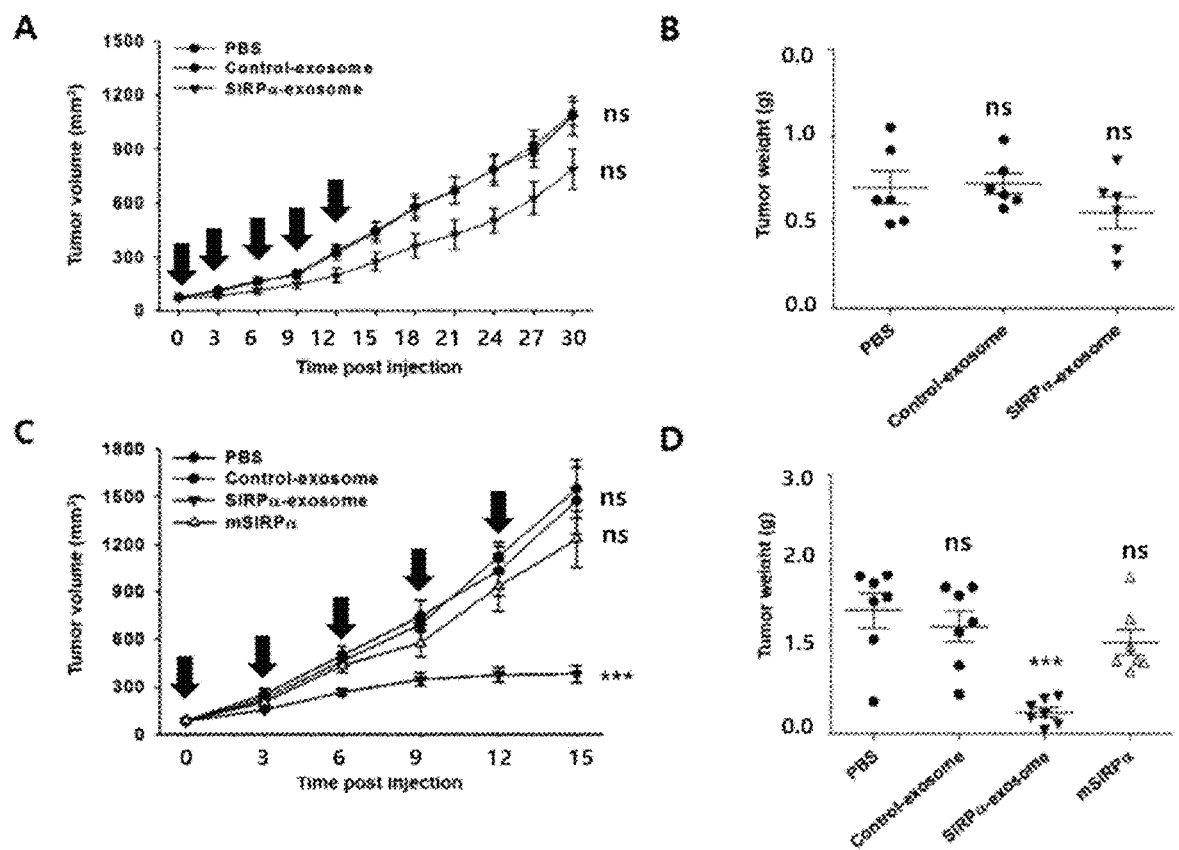
FIG. 13 represents the anti-tumor effect of SIRPα-exosomes according to an embodiment of the present invention using immuno-deficient and immunocompetent mice: (A) a graph showing an analysis of tumor growth inhibition in HT29 tumor-bearing immunodeficient BALB/c mice administered with SIRPα-exosome; (B) a graph showing the weight of excised tumors extracted from the immunodeficient mice; (C) a graph showing an analysis of tumor growth inhibition in CT26.CL25 tumor-bearing immunocompetent BALB/c mice administered with SIRPα-exosome; and a graph showing the weight of the excised tumors from the CT26.CL25 tumor-bearing mice.
Figure 14:
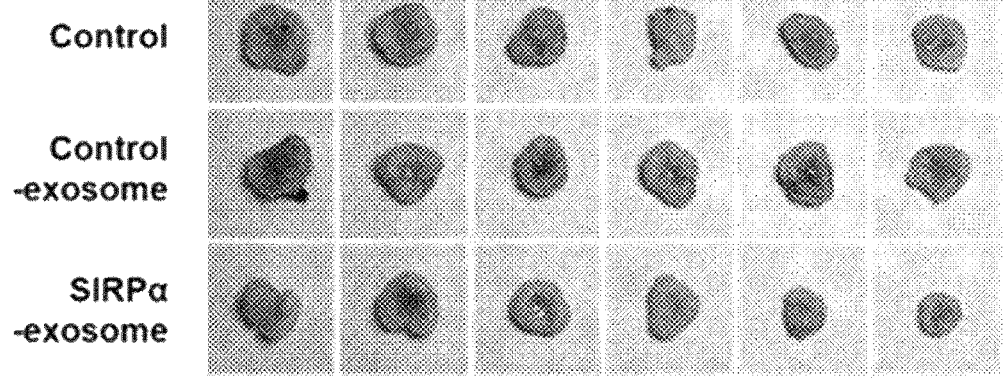
FIG. 14 represents an analysis of the antitumor effect of SIRPα-exosomes according to one embodiment of the present invention: (A) a series of photographs showing tumors excised from the HT29 mouse model; and (B) a series of photographs showing tumors excised from the CT26.CL25 tumor-bearing mouse model.
Figure 14:
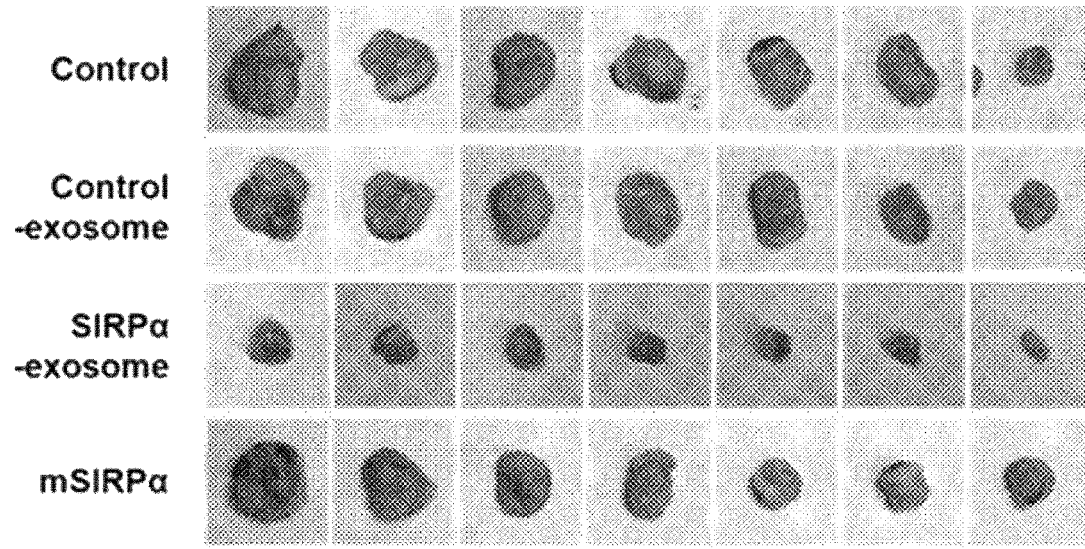
Figure 15:
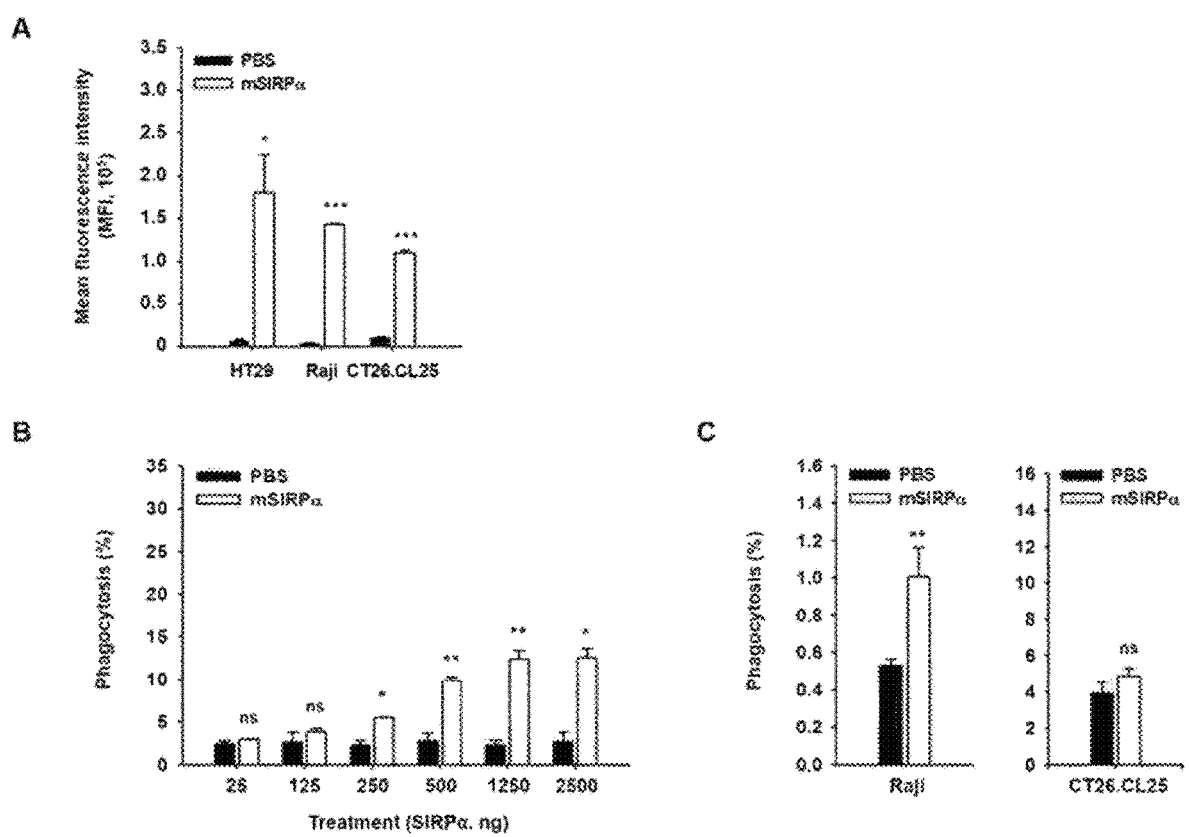
FIG. 15 represents an analysis of the antitumor effect of SIRPα-exosomes according to one embodiment of the present invention: (A) a graph showing the degree of binding monomeric SIRPα proteins to CD47; (B) a graph showing the phagocytic activity mediated by monomeric SIRPα in HT29 cells; and (C) a graph showing phagocytic activities mediated by monomeric SIRPα in Raji and CT26.CL25 cells, respectively.

As a result, the SIRPα-exosomes labeled with Cy5.5 dye were continuously accumulated in the tumor site, indicating that not only the interaction with CD47 overexpressed in tumor cells but also the permeability and retention effect of nanoparticle-like exosomes were improved (FIG. 11). In addition, ex vivo image analysis showed that Cy5.5-labeled exosomes accumulated in the liver and kidney of the mice, supporting the results of whole animal imaging analysis (FIG. 12). Further in vivo anti-cancer effect of SIRPα-exosomes in immune-deficient mice were compared with that of the control group, but tumor growth did not show significant difference. On the other hand, anti-tumor effects of SIRPα-exosome injection were analyzed in immunocompetent mice in addition to immune-deficient mice. As a result, SIRPα-exosome slightly reduced tumor growth but was not significant, whereas the administration of SIRPα-exosomes in CT26.CL25 tumor-bearing immunocompetent BALB/c mice showed a very good anti-tumor effect. This demonstrates the remarkable anti-tumor effect of SIRPα-exosomes via immune function by administration of the SIRPα-exosomes of the present invention (FIGS. 13 and 14). On the other hand, administration of the recombinant SIRPα protein (mSIRPα) did not induce the phagocytosis of the tumor properly (FIG. 15), although it could efficiently bind CD47 of cancer cells.

In conclusion, the recombinant exosome (SIRPα-exosomes) prepared according to one embodiment of the present invention blocks the CD47-SIRPα interaction and thus increases the phagocytosis of tumor cells by macrophages and dendritic cells, and thus it can be used as a novel anticancer agent for cancer treatment.

The present disclosure has been described with reference to embodiments, but it is to be understood that they are provided herein for illustrative purposes and various changes and equivalent embodiments are possible without departing from the scope of the present disclosure by those skilled in the art. Accordingly, the true scope of protection of the present disclosure should be determined by the technical concept of the appended claims.

What is claimed is:

1. A recombinant exosome in which a phagocytosis promoting protein comprising a signal regulatory protein (SIRP) comprising the amino acid sequence of any one of SEQ ID Nos. 1-61 is presented on the surface thereof.

2. The recombinant exosome according to claim 1, wherein the SIRP is comprised in a fusion protein that further comprises a receptor tyrosine kinase, wherein the SIRP is linked to the N-terminus of the transmembrane domain of the receptor tyrosine kinase.

3. The recombinant exosome according to claim 2, wherein the receptor tyrosine kinase is selected from a platelet-derived growth factor receptor (PDGFR), an epidermal growth factor receptor (EGFR), a fibroblast growth factor receptor (FGFR), a vascular endothelial growth factor receptor (VEGFR), a hepatocyte growth factor receptor tropomyosin receptor kinase, an insulin receptor (IR), a leukocyte receptor tyrosine kinase (LTK), an angiopoietin receptor, a receptor tyrosine kinase-like orphan receptor (ROR), a discoidin domain receptor (DDR), a rearranged during transfection receptor (RETR), a tyrosine-protein kinase-like (PTK), a related to receptor tyrosine kinase (RYK), and a muscle-specific kinase (MuSK).

4. The recombinant exosome according to claim 1, wherein the exosome further comprises an anticancer agent therein.

5. The recombinant exosome according to claim 4, wherein the anticancer agent is an anticancer protein or an anti-cancer compound.

6. The recombinant exosome according to claim 4, wherein the anticancer agent is selected from an asparaginase, a protein toxin, an antibody specific for a cancer antigen, an anti-cancer antigen-binding fragment of an antibody specific for a cancer antigen, a tumor suppressor gene, and an antiangiogenic factor.

7. The recombinant exosome according to claim 4, wherein the anticancer agent is selected from methotrexate, pyrimidine analogs, hydroxyurea, purine analogs, alkylating agents, immunogenic apoptosis inducing agents, mitotic inhibitors, neovascular inhibitors, intercalating agents, and radionuclides.

8. The recombinant exosome according to claim 4, wherein the anticancer agent is an immunogenic cell death inducer selected from an anthracycline anticancer agent, anti-EGFR antibody, a BK channel agonist, bortezomib, cardiac glycoside+a non-immunogenic cell death inducer, a cyclophosphamide anticancer agent, a GADD34/PP1 inhibitor+mitomycin, LV-tSMAC, Measles virus, and oxaliplatin.

9. The recombinant exosome according to claim 4, wherein the anticancer agent is at least one anthracycline anticancer agent selected from daunorubicin, doxorubicin, epirubicin, idarubicin, pixantrone, sabarubicin, and valrubicin.

10. A pharmaceutical composition for treating cancer in a subject comprising a therapeutically effective amount of a recombinant exosome of claim 1 and a pharmaceutically acceptable carrier.

11. The pharmaceutical composition according to claim 10, further comprising at least one anticancer agent.

12. A method of treating cancer in a subject in need thereof, comprising administering a therapeutically effective amount of the recombinant exosome of claim 1 to the subject.

* * * * *

SEQUENCE LISTING

```
<160> NUMBER OF SEQ ID NOS: 68

<210> SEQ ID NO 1
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 1

Glu Glu Glu Leu Gln Ile Ile Gln Pro Asp Lys Ser Val Leu Val Ala
1               5                   10                  15
```

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gly Pro Phe Pro Arg Val Thr Thr Val Ser
 50                  55                  60

Asp Thr Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
               100                 105                 110

Ser Val Arg Ala Lys Pro
            115

<210> SEQ ID NO 2
<211> LENGTH: 118
<212> TYPE: PRT
<213> ORGANISM: Artificial Sequence
<220> FEATURE:
<223> OTHER INFORMATION: human wild type SIRP alpha

<400> SEQUENCE: 2

Glu Glu Glu Leu Gln Val Ile Gln Pro Asp Lys Ser Val Leu Val Ala
 1               5                  10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
               100                 105                 110

Ser Val Arg Ala Lys Pro
            115

<210> SEQ ID NO 3
<211> LENGTH: 119
<212> TYPE: PRT
<213> ORGANISM: Artificial Sequence
<220> FEATURE:
<223> OTHER INFORMATION: wild type SIRP gamma

<400> SEQUENCE: 3

Glu Glu Glu Leu Gln Met Ile Gln Pro Glu Lys Leu Leu Leu Val Thr
 1               5                  10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
 50                  55                  60

Asp Leu Thr Lys Arg Asn Asn Met Asp Phe Ser Ile Arg Ile Ser Ser

```
            65                  70                  75                  80
Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser
            115

<210> SEQ ID NO 4
<211> LENGTH: 118
<212> TYPE: PRT
<213> ORGANISM: Artificial Sequence
<220> FEATURE:
<223> OTHER INFORMATION: SIRP gamma variant 1 (V1)

<400> SEQUENCE: 4

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
                20                  25                  30

Val Gly Pro Val Leu Trp Phe Arg Gly Val Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro
            115

<210> SEQ ID NO 5
<211> LENGTH: 118
<212> TYPE: PRT
<213> ORGANISM: Artificial Sequence
<220> FEATURE:
<223> OTHER INFORMATION: SIRP gamma variant 2 (V2)

<400> SEQUENCE: 5

Glu Glu Glu Leu Gln Ile Ile Gln Pro Glu Lys Leu Leu Leu Val Thr
1               5                   10                  15

Val Gly Lys Thr Ala Thr Leu His Cys Thr Val Thr Ser Leu Phe Pro
                20                  25                  30

Val Gly Pro Val Leu Trp Phe Arg Gly Val Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro
            115
```

<210> SEQ ID NO 6
<211> LENGTH: 117
<212> TYPE: PRT
<213> ORGANISM: Artificial Sequence
<220> FEATURE:
<223> OTHER INFORMATION: SiRP alpha variant

<400> SEQUENCE: 6

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Ile Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro
        115

<210> SEQ ID NO 7
<211> LENGTH: 117
<212> TYPE: PRT
<213> ORGANISM: Artificial Sequence
<220> FEATURE:
<223> OTHER INFORMATION: SiRP alpha D1 domain

<400> SEQUENCE: 7

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro
        115

<210> SEQ ID NO 8
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 8

Glu Glu Glu Val Gln Ile Ile Gln Pro Asp Lys Ser Val Ser Val Ala

```
             1               5                  10                 15
           Ala Gly Glu Ser Ala Ile Leu His Cys Thr Ile Thr Ser Leu Phe Pro
                            20                 25                 30

Val Gly Pro Ile Gln Trp Phe Arg Gly Ala Gly Pro Ala Arg Val Leu
                        35                 40                 45

Ile Tyr Asn Gln Arg Gln Gly Pro Phe Pro Arg Val Thr Thr Ile Ser
                    50                 55                 60

Glu Thr Thr Arg Arg Glu Asn Met Asp Phe Ser Ile Ser Ile Ser Asn
            65                 70                 75                 80

Ile Thr Pro Ala Asp Ala Gly Thr Tyr Tyr Cys Ile Lys Phe Arg Lys
                            85                 90                 95

Gly Ser Pro Asp Thr Glu Phe Lys Ser Gly Ala Gly Thr Glu Leu Ser
                        100                105                110

Val Arg Ala Lys Pro Ser
                    115

<210> SEQ ID NO 9
<211> LENGTH: 119
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (1)
<223> OTHER INFORMATION: unknown amino acid

<400> SEQUENCE: 9

Xaa Leu Leu Phe Asn Lys Thr Lys Ser Val Glu Phe Thr Phe Gly Asn
            1               5                  10                 15

Asp Thr Val Val Ile Pro Cys Phe Val Thr Asn Met Glu Ala Gln Asn
                            20                 25                 30

Thr Thr Glu Val Tyr Val Lys Trp Lys Phe Lys Gly Arg Asp Ile Tyr
                        35                 40                 45

Thr Phe Asp Gly Ala Leu Asn Lys Ser Thr Val Pro Thr Asp Phe Ser
                    50                 55                 60

Ser Ala Lys Ile Glu Val Ser Gln Leu Leu Lys Gly Asp Ala Ser Leu
            65                 70                 75                 80

Lys Met Asp Lys Ser Asp Ala Val Ser His Thr Gly Asn Tyr Thr Cys
                            85                 90                 95

Glu Val Thr Glu Leu Thr Arg Glu Gly Glu Thr Ile Ile Glu Leu Lys
                        100                105                110

Tyr Arg Val Val Ser Thr Arg
                    115

<210> SEQ ID NO 10
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 10

Glu Glu Glu Val Gln Ile Gln Pro Asp Lys Ser Val Ser Val Ala
            1               5                  10                 15

Ala Gly Glu Ser Ala Ile Leu His Cys Thr Ile Thr Ser Leu Phe Pro
                            20                 25                 30

Val Gly Pro Ile Gln Trp Phe Arg Gly Ala Gly Pro Ala Arg Val Leu
                        35                 40                 45
```

Ile Tyr Asn Gln Arg Gln Gly Pro Phe Pro Arg Val Thr Thr Ile Ser
 50                  55                  60

Glu Thr Thr Arg Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 11
<211> LENGTH: 121
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (1)
<223> OTHER INFORMATION: unknown amino acid

<400> SEQUENCE: 11

Xaa Leu Leu Phe Asn Lys Thr Lys Ser Val Glu Phe Thr Phe Gly Asn
 1               5                  10                  15

Asp Thr Val Val Ile Pro Cys Phe Val Thr Asn Met Glu Ala Gln Asn
                 20                  25                  30

Thr Thr Glu Val Tyr Val Lys Trp Lys Phe Lys Gly Arg Asp Ile Tyr
             35                  40                  45

Thr Phe Asp Gly Ala Leu Asn Lys Ser Thr Val Pro Thr Asp Phe Ser
 50                  55                  60

Ser Ala Lys Ile Glu Val Ser Gln Leu Leu Lys Gly Asp Ala Ser Leu
 65                  70                  75                  80

Lys Met Asp Lys Ser Asp Ala Val Ser His Thr Gly Asn Tyr Thr Cys
                 85                  90                  95

Glu Val Thr Glu Leu Thr Arg Glu Gly Glu Thr Ile Ile Glu Leu Lys
                100                 105                 110

Tyr Arg Val Val Ser Trp Ser Thr Arg
            115                 120

<210> SEQ ID NO 12
<211> LENGTH: 120
<212> TYPE: PRT
<213> ORGANISM: Artificial Sequence
<220> FEATURE:
<223> OTHER INFORMATION: SiRP alpha variant

<400> SEQUENCE: 12

Glu Glu Glu Leu Gln Val Ile Gln Pro Asp Lys Ser Val Ser Val Ala
 1               5                  10                  15

Ala Gly Glu Ser Ala Ile Leu His Cys Thr Val Thr Ser Leu Ile Pro
                 20                  25                  30

Val Gly Pro Ile Gln Trp Phe Arg Gly Ala Gly Pro Ala Arg Glu Leu
             35                  40                  45

Ile Tyr Asn Gln Lys Glu Gly His Phe Pro Arg Val Thr Thr Val Ser
 50                  55                  60

Glu Ser Thr Lys Arg Glu Asn Met Asp Phe Ser Ile Ser Ile Ser Asn
 65                  70                  75                  80

```
Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Thr Arg
        115                 120

<210> SEQ ID NO 13
<211> LENGTH: 120
<212> TYPE: PRT
<213> ORGANISM: Artificial Sequence
<220> FEATURE:
<223> OTHER INFORMATION: SiRP alpha variant

<400> SEQUENCE: 13

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Thr Arg
        115                 120

<210> SEQ ID NO 14
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 14

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly His Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 15
```

```
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 15

Glu Glu Glu Val Gln Val Ile Gln Pro Asp Lys Ser Val Ser Val Ala
1               5                   10                  15

Ala Gly Glu Ser Ala Ile Leu His Cys Thr Leu Thr Ser Leu Ile Pro
            20                  25                  30

Val Gly Pro Ile Gln Trp Phe Arg Gly Ala Gly Pro Ala Arg Val Leu
        35                  40                  45

Ile Tyr Asn Gln Arg Gly His Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 16
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 16

Glu Glu Glu Val Gln Ile Ile Gln Pro Asp Lys Ser Val Ser Val Ala
1               5                   10                  15

Ala Gly Glu Ser Val Ile Leu His Cys Thr Ile Thr Ser Leu Thr Pro
            20                  25                  30

Val Gly Pro Ile Gln Trp Phe Arg Gly Ala Gly Pro Ala Arg Leu Leu
        35                  40                  45

Ile Tyr Asn Gln Arg Glu Gly Pro Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 17
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 17

Glu Glu Glu Leu Gln Ile Ile Gln Pro Asp Lys Ser Val Ser Val Ala
1               5                   10                  15
```

```
Ala Gly Glu Ser Ala Ile Leu His Cys Thr Ile Thr Ser Leu Ser Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 18
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 18

Glu Glu Glu Ile Gln Val Ile Gln Pro Asp Lys Ser Val Ser Val Ala
1               5                   10                  15

Ala Gly Glu Ser Val Ile Ile His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Arg Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Val Arg Lys
                85                  90                  95

Gly Ser Pro Asp Thr Glu Val Lys Ser Gly Ala Gly Thr Glu Leu Ser
                100                 105                 110

Val Arg Ala Lys Pro Ser
            115

<210> SEQ ID NO 19
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 19

Glu Glu Glu Val Gln Ile Ile Gln Pro Asp Lys Ser Val Ser Val Ala
1               5                   10                  15

Ala Gly Glu Ser Ile Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Arg Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80
```

Ile Thr Pro Ala Asp Ala Gly Thr Tyr Tyr Cys Ile Lys Leu Arg Lys
            85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 20
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 20

Glu Glu Glu Val Gln Leu Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
            35                  40                  45

Ile Tyr Asn Gln Arg Glu Gly Pro Phe Pro Arg Val Thr Thr Val Ser
        50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
            85                  90                  95

Gly Ser Pro Asp Thr Glu Val Lys Ser Gly Ala Gly Thr Glu Leu Ser
            100                 105                 110

Val Arg Ala Lys Pro Ser
            115

<210> SEQ ID NO 21
<211> LENGTH: 119
<212> TYPE: PRT
<213> ORGANISM: Artificial Sequence
<220> FEATURE:
<223> OTHER INFORMATION: SiRP alpha variant

<400> SEQUENCE: 21

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
            115

```
<210> SEQ ID NO 22
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 22
```

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Leu Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

```
<210> SEQ ID NO 23
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 23
```

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Lys Gln Gly Pro Phe Pro Arg Val Thr Thr Ile Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

```
<210> SEQ ID NO 24
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 24
```

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Thr Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 25
<211> LENGTH: 119
<212> TYPE: PRT
<213> ORGANISM: Artificial Sequence
<220> FEATURE:
<223> OTHER INFORMATION: SiRP alpha variant

<400> SEQUENCE: 25

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 26
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 26

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn

```
            65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
                115

<210> SEQ ID NO 27
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 27

Glu Glu Glu Leu Gln Val Ile Gln Pro Asp Lys Ser Val Ser Val Ala
1               5                   10                  15

Ala Gly Glu Ser Ala Ile Leu Leu Cys Thr Val Thr Ser Leu Ile Pro
                20                  25                  30

Val Gly Pro Ile Gln Trp Phe Arg Gly Ala Gly Pro Ala Arg Glu Leu
                35                  40                  45

Ile Tyr Asn Gln Lys Glu Gly His Phe Pro Arg Val Thr Thr Val Ser
            50                  55                  60

Glu Ser Thr Lys Arg Glu Asn Met Asp Phe Ser Ile Ser Ile Ser Asn
65              70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
                115

<210> SEQ ID NO 28
<211> LENGTH: 119
<212> TYPE: PRT
<213> ORGANISM: Artificial Sequence
<220> FEATURE:
<223> OTHER INFORMATION: SiRP alpha variant

<400> SEQUENCE: 28

Glu Glu Gly Leu Gln Val Ile Gln Pro Asp Lys Ser Val Ser Val Ala
1               5                   10                  15

Ala Gly Glu Ser Ala Ile Leu His Cys Thr Ala Thr Ser Leu Ile Pro
                20                  25                  30

Val Gly Pro Ile Gln Trp Phe Arg Gly Ala Gly Pro Gly Arg Glu Leu
                35                  40                  45

Ile Tyr Asn Gln Lys Glu Gly His Phe Pro Arg Val Thr Thr Val Ser
            50                  55                  60

Asp Leu Thr Lys Arg Asn Asn Met Asp Phe Ser Ile Arg Ile Gly Asn
65              70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
                115
```

<210> SEQ ID NO 29
<211> LENGTH: 119
<212> TYPE: PRT
<213> ORGANISM: Artificial Sequence
<220> FEATURE:
<223> OTHER INFORMATION: SiRP alpha variant

<400> SEQUENCE: 29

```
Glu Glu Glu Leu Gln Val Ile Gln Pro Asp Lys Phe Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 30
<211> LENGTH: 119
<212> TYPE: PRT
<213> ORGANISM: Artificial Sequence
<220> FEATURE:
<223> OTHER INFORMATION: SiRP alpha variant

<400> SEQUENCE: 30

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Pro Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 31
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 31

```
Glu Glu Glu Leu Gln Val Ile Gln Pro Asp Lys Ser Val Ser Val Ala
```

```
                1               5                   10                  15
Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
                35                  40                  45

Ile Tyr Asn Gln Lys Glu Gly His Phe Pro Arg Val Thr Thr Val Ser
                50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Gly Lys Pro Ser
                115

<210> SEQ ID NO 32
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 32

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
                20                  25                  30

Val Gly Pro Ile Gln Trp Phe Arg Gly Ala Gly Pro Ala Arg Glu Leu
                35                  40                  45

Ile Tyr Asn Gln Lys Glu Gly His Phe Pro Arg Val Thr Thr Val Ser
                50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
                115

<210> SEQ ID NO 33
<211> LENGTH: 119
<212> TYPE: PRT
<213> ORGANISM: Artificial Sequence
<220> FEATURE:
<223> OTHER INFORMATION: SiRP alpha variant

<400> SEQUENCE: 33

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
                20                  25                  30

Val Gly Pro Ile Gln Trp Phe Arg Gly Ala Gly Pro Gly Arg Glu Leu
                35                  40                  45

Ile Tyr Asn Gln Lys Glu Gly His Phe Pro Arg Val Thr Thr Val Ser
                50                  55                  60
```

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 34
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 34

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 35
<211> LENGTH: 119
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT

```
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (104)
<223> OTHER INFORMATION: unknown amino acid

<400> SEQUENCE: 35

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
            115

<210> SEQ ID NO 36
<211> LENGTH: 118
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
```

<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (103)
<223> OTHER INFORMATION: unknown amino acid

<400> SEQUENCE: 36

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
            115

<210> SEQ ID NO 37
<211> LENGTH: 118

```
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (103)
<223> OTHER INFORMATION: unknown amino acid

<400> SEQUENCE: 37

Glu Glu Glu Xaa Gln Xaa Ile Gln Pro Asp Lys Ser Val Ser Val Ala
1               5                   10                  15

Ala Gly Glu Ser Xaa Ile Leu Leu Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60
```

```
Glu Xaa Thr Xaa Arg Glu Asn Met Asp Phe Ser Ile Ser Ile Ser Xaa
 65      70                  75                  80

Ile Thr Xaa Ala Asp Ala Gly Thr Tyr Tyr Cys Xaa Lys Xaa Arg Lys
             85                  90                  95

Gly Ser Pro Asp Thr Glu Xaa Lys Ser Gly Ala Gly Thr Glu Leu Ser
            100                 105                 110

Val Arg Ala Lys Pro Ser
            115

<210> SEQ ID NO 38
<211> LENGTH: 119
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (104)
<223> OTHER INFORMATION: unknown amino acid
```

<400> SEQUENCE: 38

Glu Glu Gly Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Gly Arg Xaa Leu
            35                  40                  45

Ile Tyr Asn Gln Xaa Xaa Gly Xaa Phe Pro Arg Val Thr Thr Val Ser
50                  55                  60

Asp Xaa Thr Xaa Arg Asn Asn Met Asp Phe Ser Ile Arg Ile Gly Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
            115

<210> SEQ ID NO 39
<211> LENGTH: 119
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:

```
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (104)
<223> OTHER INFORMATION: unknown amino acid

<400> SEQUENCE: 39

Glu Glu Glu Xaa Gln Xaa Ile Gln Pro Asp Lys Phe Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 40
<211> LENGTH: 119
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
```

```
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (104)
<223> OTHER INFORMATION: unknown amino acid

<400> SEQUENCE: 40

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Pro Ile Arg Ile Gly Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
        100                 105                 110

Ser Val Arg Ala Lys Pro Ser
        115

<210> SEQ ID NO 41
<211> LENGTH: 118
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
<223> OTHER INFORMATION: unknown amino acid
<220> FEATURE:
<221> NAME/KEY: VARIANT
<222> LOCATION: (27)
```

```
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (103)
<223> OTHER INFORMATION: unknown amino acid

<400> SEQUENCE: 41

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Gly Lys Pro Ser
        115

<210> SEQ ID NO 42
<211> LENGTH: 118
<212> TYPE: PRT
<213> ORGANISM: Artificial Sequence
<220> FEATURE:
<223> OTHER INFORMATION: SiRP alpha variant
```

```
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (103)
<223> OTHER INFORMATION: unknown amino acid

<400> SEQUENCE: 42

Glu Glu Glu Xaa Gln Xaa Ile Gln Pro Asp Lys Ser Val Leu Val Ala
 1               5                  10                  15

Ala Gly Glu Thr Xaa Thr Leu Arg Cys Thr Xaa Thr Ser Leu Xaa Pro
             20                  25                  30

Val Gly Pro Ile Gln Trp Phe Arg Gly Ala Gly Pro Ala Arg Xaa Leu
         35                  40                  45

Ile Tyr Asn Gln Xaa Xaa Gly Xaa Phe Pro Arg Val Thr Thr Val Ser
     50                  55                  60

Glu Xaa Thr Xaa Arg Glu Asn Met Asp Phe Ser Ile Ser Ile Ser Xaa
 65                  70                  75                  80

Ile Thr Xaa Ala Asp Ala Gly Thr Tyr Tyr Cys Xaa Lys Xaa Arg Lys
```

```
                 85                  90                  95
Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 43
<211> LENGTH: 119
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (104)
<223> OTHER INFORMATION: unknown amino acid

<400> SEQUENCE: 43

Glu Glu Glu Xaa Gln Xaa Ile Gln Pro Asp Lys Ser Val Leu Val Ala
```

```
  1               5                  10                  15
Ala Gly Glu Thr Xaa Thr Leu Arg Cys Thr Xaa Thr Ser Leu Xaa Pro
         20                  25                  30

Val Gly Pro Ile Gln Trp Phe Arg Gly Ala Gly Pro Gly Arg Xaa Leu
         35                  40                  45

Ile Tyr Asn Gln Xaa Xaa Gly Xaa Phe Pro Arg Val Thr Thr Val Ser
     50                  55                  60

Asp Xaa Thr Xaa Arg Asn Asn Met Asp Phe Ser Ile Arg Ile Ser Xaa
 65                  70                  75                  80

Ile Thr Xaa Ala Asp Ala Gly Thr Tyr Tyr Cys Xaa Lys Xaa Arg Lys
             85                  90                  95

Gly Ser Pro Asp Asp Val Glu Xaa Lys Ser Gly Ala Gly Thr Glu Leu
            100                 105                 110

Ser Val Arg Ala Lys Pro Ser
            115
```

<210> SEQ ID NO 44
<211> LENGTH: 118
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (21)
<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:

```
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (103)
<223> OTHER INFORMATION: unknown amino acid

<400> SEQUENCE: 44

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 45
<211> LENGTH: 119
<212> TYPE: PRT
<213> ORGANISM: Artificial Sequence
<220> FEATURE:
<223> OTHER INFORMATION: SiRP alpha variant
<220> FEATURE:
<221> NAME/KEY: VARIANT
<222> LOCATION: (3)..(4)
<223> OTHER INFORMATION: unknown amino acid
<220> FEATURE:
<221> NAME/KEY: VARIANT
<222> LOCATION: (6)
<223> OTHER INFORMATION: unknown amino acid
<220> FEATURE:
<221> NAME/KEY: VARIANT
<222> LOCATION: (12)
<223> OTHER INFORMATION: unknown amino acid
<220> FEATURE:
<221> NAME/KEY: VARIANT
<222> LOCATION: (14)
<223> OTHER INFORMATION: unknown amino acid
<220> FEATURE:
<221> NAME/KEY: VARIANT
<222> LOCATION: (20)..(22)
<223> OTHER INFORMATION: unknown amino acid
<220> FEATURE:
<221> NAME/KEY: VARIANT
<222> LOCATION: (24)
<223> OTHER INFORMATION: unknown amino acid
<220> FEATURE:
<221> NAME/KEY: VARIANT
<222> LOCATION: (27)
<223> OTHER INFORMATION: unknown amino acid
<220> FEATURE:
<221> NAME/KEY: VARIANT
<222> LOCATION: (31)
<223> OTHER INFORMATION: unknown amino acid
<220> FEATURE:
<221> NAME/KEY: VARIANT
```

```
<222> LOCATION: (45)
<223> OTHER INFORMATION: unknown amino acid
<220> FEATURE:
<221> NAME/KEY: VARIANT
<222> LOCATION: (47)
<223> OTHER INFORMATION: unknown amino acid
<220> FEATURE:
<221> NAME/KEY: VARIANT
<222> LOCATION: (53)..(54)
<223> OTHER INFORMATION: unknown amino acid
<220> FEATURE:
<221> NAME/KEY: VARIANT
<222> LOCATION: (56)
<223> OTHER INFORMATION: unknown amino acid
<220> FEATURE:
<221> NAME/KEY: VARIANT
<222> LOCATION: (65)..(66)
<223> OTHER INFORMATION: unknown amino acid
<220> FEATURE:
<221> NAME/KEY: VARIANT
<222> LOCATION: (68)
<223> OTHER INFORMATION: unknown amino acid
<220> FEATURE:
<221> NAME/KEY: VARIANT
<222> LOCATION: (70)
<223> OTHER INFORMATION: unknown amino acid
<220> FEATURE:
<221> NAME/KEY: VARIANT
<222> LOCATION: (75)
<223> OTHER INFORMATION: unknown amino acid
<220> FEATURE:
<221> NAME/KEY: VARIANT
<222> LOCATION: (77)
<223> OTHER INFORMATION: unknown amino acid
<220> FEATURE:
<221> NAME/KEY: VARIANT
<222> LOCATION: (79)..(80)
<223> OTHER INFORMATION: unknown amino acid
<220> FEATURE:
<221> NAME/KEY: VARIANT
<222> LOCATION: (83)
<223> OTHER INFORMATION: unknown amino acid
<220> FEATURE:
<221> NAME/KEY: VARIANT
<222> LOCATION: (92)
<223> OTHER INFORMATION: unknown amino acid
<220> FEATURE:
<221> NAME/KEY: VARIANT
<222> LOCATION: (94)
<223> OTHER INFORMATION: unknown amino acid
<220> FEATURE:
<221> NAME/KEY: VARIANT
<222> LOCATION: (101)..(102)
<223> OTHER INFORMATION: unknown amino acid
<220> FEATURE:
<221> NAME/KEY: VARIANT
<222> LOCATION: (104)
<223> OTHER INFORMATION: unknown amino acid
<220> FEATURE:
<221> NAME/KEY: VARIANT
<222> LOCATION: (116)
<223> OTHER INFORMATION: unknown amino acid

<400> SEQUENCE: 45

Glu Glu Xaa Xaa Gln Xaa Ile Gln Pro Asp Lys Xaa Val Xaa Val Ala
1               5                   10                  15

Ala Gly Glu Xaa Xaa Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
    50                  55                  60

Xaa Xaa Thr Xaa Arg Xaa Asn Met Asp Phe Xaa Ile Xaa Ile Xaa Xaa
65                  70                  75                  80
```

```
Ile Thr Xaa Ala Asp Ala Gly Thr Tyr Tyr Cys Xaa Lys Xaa Arg Lys
                85                  90                  95

Gly Ser Pro Asp Xaa Xaa Glu Xaa Lys Ser Gly Ala Gly Thr Glu Leu
            100             105                 110

Ser Val Arg Xaa Lys Pro Ser
            115
```

<210> SEQ ID NO 46
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 46

```
Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly His Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
            115
```

<210> SEQ ID NO 47
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 47

```
Glu Glu Glu Val Gln Val Ile Gln Pro Asp Lys Ser Val Ser Val Ala
1               5                   10                  15

Ala Gly Glu Ser Ala Ile Leu His Cys Thr Leu Thr Ser Leu Ile Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly His Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115
```

```
<210> SEQ ID NO 48
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 48

Glu Glu Glu Val Gln Ile Ile Gln Pro Asp Lys Ser Val Ser Val Ala
 1               5                  10                  15

Ala Gly Glu Ser Val Ile Leu His Cys Thr Ile Thr Ser Leu Thr Pro
            20                  25                  30

Val Gly Pro Ile Gln Trp Phe Arg Gly Ala Gly Pro Ala Arg Leu Leu
        35                  40                  45

Ile Tyr Asn Gln Arg Glu Gly Pro Phe Pro Arg Val Thr Thr Val Ser
 50                  55                  60

Glu Thr Thr Arg Arg Glu Asn Met Asp Phe Ser Ile Ser Ile Ser Asn
 65                  70                  75                  80

Ile Thr Pro Ala Asp Ala Gly Thr Tyr Tyr Cys Val Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 49
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 49

Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Ser Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
 50                  55                  60

Glu Gly Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 50
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 50

Glu Glu Glu Ile Gln Val Ile Gln Pro Asp Lys Ser Val Ser Val Ala
 1               5                  10                  15
```

Ala Gly Glu Ser Val Ile Ile His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Arg Phe Pro Arg Val Thr Thr Val Ser
 50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Val Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
            115

<210> SEQ ID NO 51
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 51

Glu Glu Glu Val Gln Ile Ile Gln Pro Asp Lys Ser Val Ser Val Ala
1               5                   10                  15

Ala Gly Glu Ser Ile Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Arg Phe Pro Arg Val Thr Thr Val Ser
 50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 52
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 52

Glu Glu Glu Val Gln Leu Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Pro Phe Pro Arg Val Thr Thr Val Ser
 50                  55                  60

Glu Gly Thr Lys Arg Glu Asn Met Asp Phe Ser Ile Ser Ile Ser Asn

```
                65                  70                  75                  80
Ile Thr Pro Ala Asp Ala Gly Thr Tyr Tyr Cys Ile Lys Phe Arg Lys
                    85                  90                  95

Gly Ser Pro Asp Thr Glu Val Lys Ser Gly Ala Gly Thr Glu Leu Ser
                100                 105                 110

Val Arg Ala Lys Pro Ser
            115
```

<210> SEQ ID NO 53
<211> LENGTH: 119
<212> TYPE: PRT
<213> ORGANISM: Artificial Sequence
<220> FEATURE:
<223> OTHER INFORMATION: SiRP alpha variant

<400> SEQUENCE: 53

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                    85                  90                  95

Gly Ser Pro Asp Asp Val Glu Phe Lys Ser Gly Ala Gly Thr Glu Leu
                100                 105                 110

Ser Val Arg Ala Lys Pro Ser
            115
```

<210> SEQ ID NO 54
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 54

```
Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Leu Leu
            35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                    85                  90                  95

Gly Ser Pro Asp Thr Glu Phe Lys Ser Gly Ala Gly Thr Glu Leu Ser
                100                 105                 110

Val Arg Ala Lys Pro Ser
            115
```

```
<210> SEQ ID NO 55
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 55

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Lys Gln Gly Pro Phe Pro Arg Val Thr Thr Ile Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 56
<211> LENGTH: 118
<212> TYPE: PRT
<213> ORGANISM: Artificial Sequence
<220> FEATURE:
<223> OTHER INFORMATION: SiRP alpha variant

<400> SEQUENCE: 56

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Thr Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 57
<211> LENGTH: 474
<212> TYPE: PRT
<213> ORGANISM: Artificial Sequence
<220> FEATURE:
<223> OTHER INFORMATION: human wild type SIRP-alpha(h-wa) full sequence

<400> SEQUENCE: 57

Glu Glu Glu Leu Gln Val Ile Gln Pro Asp Lys Ser Val Leu Val Ala
```

```
1               5                   10                  15
Ala Gly Glu Thr Ala Thr Leu Arg Cys Thr Ala Thr Ser Leu Ile Pro
                20                  25                  30
Val Gly Pro Ile Gln Trp Phe Arg Gly Ala Gly Pro Gly Arg Glu Leu
                35                  40                  45
Ile Tyr Asn Gln Lys Glu Gly His Phe Pro Arg Val Thr Thr Val Ser
                50                  55                  60
Asp Leu Thr Lys Arg Asn Asn Met Asp Phe Ser Ile Arg Ile Gly Asn
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
                100                 105                 110
Ser Val Arg Ala Lys Pro Ser Ala Pro Val Val Ser Gly Pro Ala Ala
                115                 120                 125
Arg Ala Thr Pro Gln His Thr Val Ser Phe Thr Cys Glu Ser His Gly
                130                 135                 140
Phe Ser Pro Arg Asp Ile Thr Leu Lys Trp Phe Lys Asn Gly Asn Glu
145                 150                 155                 160
Leu Ser Asp Phe Gln Thr Asn Val Asp Pro Val Gly Glu Ser Val Ser
                165                 170                 175
Tyr Ser Ile His Ser Thr Ala Lys Val Val Leu Thr Arg Glu Asp Val
                180                 185                 190
His Ser Gln Val Ile Cys Glu Val Ala His Val Thr Leu Gln Gly Asp
                195                 200                 205
Pro Leu Arg Gly Thr Ala Asn Leu Ser Glu Thr Ile Arg Val Pro Pro
210                 215                 220
Thr Leu Glu Val Thr Gln Gln Pro Val Arg Ala Glu Asn Gln Val Asn
225                 230                 235                 240
Val Thr Cys Gln Val Arg Lys Phe Tyr Pro Gln Arg Leu Gln Leu Thr
                245                 250                 255
Trp Leu Glu Asn Gly Asn Val Ser Arg Thr Glu Thr Ala Ser Thr Val
                260                 265                 270
Thr Glu Asn Lys Asp Gly Thr Tyr Asn Trp Met Ser Trp Leu Leu Val
                275                 280                 285
Asn Val Ser Ala His Arg Asp Asp Val Lys Leu Thr Cys Gln Val Glu
                290                 295                 300
His Asp Gly Gln Pro Ala Val Ser Lys Ser His Asp Leu Lys Val Ser
305                 310                 315                 320
Ala His Pro Lys Glu Gln Gly Ser Asn Thr Ala Ala Glu Asn Thr Gly
                325                 330                 335
Ser Asn Glu Arg Asn Ile Tyr Ile Val Val Gly Val Val Cys Thr Leu
                340                 345                 350
Leu Val Ala Leu Leu Met Ala Ala Leu Tyr Leu Val Arg Ile Arg Gln
                355                 360                 365
Lys Lys Ala Gln Gly Ser Thr Ser Ser Thr Arg Leu His Glu Pro Glu
                370                 375                 380
Lys Asn Ala Arg Glu Ile Thr Gln Asp Thr Asn Asp Ile Thr Tyr Ala
385                 390                 395                 400
Asp Leu Asn Leu Pro Lys Gly Lys Lys Pro Ala Pro Gln Ala Ala Glu
                405                 410                 415
Pro Asn Asn His Thr Glu Tyr Ala Ser Ile Gln Thr Ser Pro Gln Pro
                420                 425                 430
```

```
Ala Ser Glu Asp Thr Leu Thr Tyr Ala Asp Leu Asp Met Val His Leu
        435                 440                 445

Asn Arg Thr Pro Lys Gln Pro Ala Pro Lys Pro Glu Pro Ser Phe Ser
    450                 455                 460

Glu Tyr Ala Ser Val Gln Val Pro Arg Lys
465                 470

<210> SEQ ID NO 58
<211> LENGTH: 474
<212> TYPE: PRT
<213> ORGANISM: Artificial Sequence
<220> FEATURE:
<223> OTHER INFORMATION: variant SIRP-alpha(va) full sequence

<400> SEQUENCE: 58

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320
```

```
Ala His Pro Lys Glu Gln Gly Ser Asn Thr Ala Ala Glu Asn Thr Gly
                325                 330                 335

Ser Asn Glu Arg Asn Ile Tyr Ile Val Val Gly Val Val Cys Thr Leu
            340                 345                 350

Leu Val Ala Leu Leu Met Ala Ala Leu Tyr Leu Val Arg Ile Arg Gln
        355                 360                 365

Lys Lys Ala Gln Gly Ser Thr Ser Ser Thr Arg Leu His Glu Pro Glu
    370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Lys Pro Ala Pro Gln Ala Ala Glu
                405                 410                 415

Pro Asn Asn His Thr Glu Tyr Ala Ser Ile Gln Thr Ser Pro Gln Pro
            420                 425                 430

Ala Ser Glu Asp Thr Leu Thr Tyr Ala Asp Leu Asp Met Val His Leu
        435                 440                 445

Asn Arg Thr Pro Lys Gln Pro Ala Pro Lys Pro Glu Pro Ser Phe Ser
    450                 455                 460

Glu Tyr Ala Ser Val Gln Val Pro Arg Lys
465                 470

<210> SEQ ID NO 59
<211> LENGTH: 359
<212> TYPE: PRT
<213> ORGANISM: Artificial Sequence
<220> FEATURE:
<223> OTHER INFORMATION: wild type SIRP-gamma(wg) full sequence

<400> SEQUENCE: 59

Glu Glu Glu Leu Gln Met Ile Gln Pro Glu Lys Leu Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser Ala Pro Val Val Leu Gly Pro Ala Ala
        115                 120                 125

Arg Thr Thr Pro Glu His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Thr Gly Gln Ser Val Ala
                165                 170                 175

Tyr Ser Ile Arg Ser Thr Ala Arg Val Val Leu Asp Pro Trp Asp Val
            180                 185                 190

Arg Ser Gln Val Ile Cys Glu Val Ala His Val Thr Leu Gln Gly Asp
        195                 200                 205
```

```
Pro Leu Arg Gly Thr Ala Asn Leu Ser Glu Ala Ile Arg Val Pro Pro
    210                 215                 220

Thr Leu Glu Val Thr Gln Gln Pro Met Arg Val Gly Asn Gln Val Asn
225                 230                 235                 240

Val Thr Cys Gln Val Arg Lys Phe Tyr Pro Gln Ser Leu Gln Leu Thr
                245                 250                 255

Trp Ser Glu Asn Gly Asn Val Cys Gln Arg Glu Thr Ala Ser Thr Leu
                260                 265                 270

Thr Glu Asn Lys Asp Gly Thr Tyr Asn Trp Thr Ser Trp Phe Leu Val
            275                 280                 285

Asn Ile Ser Asp Gln Arg Asp Val Val Leu Thr Cys Gln Val Lys
        290                 295                 300

His Asp Gly Gln Leu Ala Val Ser Lys Arg Leu Ala Leu Glu Val Thr
305                 310                 315                 320

Val His Gln Lys Asp Gln Ser Ser Asp Ala Thr Pro Gly Pro Ala Ser
                325                 330                 335

Ser Leu Thr Ala Leu Leu Leu Ile Ala Val Leu Leu Gly Pro Ile Tyr
                340                 345                 350

Val Pro Trp Lys Gln Lys Thr
            355
```

<210> SEQ ID NO 60
<211> LENGTH: 358
<212> TYPE: PRT
<213> ORGANISM: Artificial Sequence
<220> FEATURE:
<223> OTHER INFORMATION: variant SIRP-gamma-1 (vg-1) full sequence

<400> SEQUENCE: 60

```
Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
            20                  25                  30

Val Gly Pro Val Leu Trp Phe Arg Gly Val Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ala Pro Val Val Leu Gly Pro Ala Ala Arg
        115                 120                 125

Thr Thr Pro Glu His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Phe Gln Thr Asn Val Asp Pro Thr Gly Gln Ser Val Ala Tyr
                165                 170                 175

Ser Ile Arg Ser Thr Ala Arg Val Val Leu Asp Pro Trp Asp Val Arg
            180                 185                 190

Ser Gln Val Ile Cys Glu Val Ala His Val Thr Leu Gln Gly Asp Pro
        195                 200                 205
```

```
Leu Arg Gly Thr Ala Asn Leu Ser Glu Ala Ile Arg Val Pro Pro Thr
    210                 215                 220
Leu Glu Val Thr Gln Gln Pro Met Arg Val Gly Asn Gln Val Asn Val
225                 230                 235                 240
Thr Cys Gln Val Arg Lys Phe Tyr Pro Gln Ser Leu Gln Leu Thr Trp
                245                 250                 255
Ser Glu Asn Gly Asn Val Cys Gln Arg Glu Thr Ala Ser Thr Leu Thr
            260                 265                 270
Glu Asn Lys Asp Gly Thr Tyr Asn Trp Thr Ser Trp Phe Leu Val Asn
        275                 280                 285
Ile Ser Asp Gln Arg Asp Val Val Leu Thr Cys Gln Val Lys His
    290                 295                 300
Asp Gly Gln Leu Ala Val Ser Lys Arg Leu Ala Leu Glu Val Thr Val
305                 310                 315                 320
His Gln Lys Asp Gln Ser Ser Asp Ala Thr Pro Gly Pro Ala Ser Ser
                325                 330                 335
Leu Thr Ala Leu Leu Leu Ile Ala Val Leu Leu Gly Pro Ile Tyr Val
                340                 345                 350
Pro Trp Lys Gln Lys Thr
            355

<210> SEQ ID NO 61
<211> LENGTH: 358
<212> TYPE: PRT
<213> ORGANISM: Artificial Sequence
<220> FEATURE:
<223> OTHER INFORMATION: variant SIRP-gamma-2 (vg-2) full sequence

<400> SEQUENCE: 61

Glu Glu Glu Leu Gln Ile Ile Gln Pro Glu Lys Leu Leu Leu Val Thr
1               5                   10                  15
Val Gly Lys Thr Ala Thr Leu His Cys Thr Val Thr Ser Leu Phe Pro
                20                  25                  30
Val Gly Pro Val Leu Trp Phe Arg Gly Val Gly Pro Gly Arg Val Leu
                35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Ser Ser
65                  70                  75                  80
Ile Thr Pro Ala Asp Val Gly Thr Tyr Tyr Cys Ile Lys Phe Arg Lys
                85                  90                  95
Gly Ser Pro Glu Asn Val Glu Phe Lys Ser Gly Pro Gly Thr Glu Met
            100                 105                 110
Ala Leu Gly Ala Lys Pro Ala Pro Val Val Leu Gly Pro Ala Ala Arg
        115                 120                 125
Thr Thr Pro Glu His Thr Val Ser Phe Thr Cys Glu Ser His Gly Phe
    130                 135                 140
Ser Pro Arg Asp Ile Thr Leu Lys Trp Phe Lys Asn Gly Asn Glu Leu
145                 150                 155                 160
Ser Asp Phe Gln Thr Asn Val Asp Pro Thr Gly Gln Ser Val Ala Tyr
                165                 170                 175
Ser Ile Arg Ser Thr Ala Arg Val Val Leu Asp Pro Trp Asp Val Arg
            180                 185                 190
Ser Gln Val Ile Cys Glu Val Ala His Val Thr Leu Gln Gly Asp Pro
        195                 200                 205
```

Leu Arg Gly Thr Ala Asn Leu Ser Glu Ala Ile Arg Val Pro Pro Thr
    210                 215                 220

Leu Glu Val Thr Gln Gln Pro Met Arg Val Gly Asn Gln Val Asn Val
225                 230                 235                 240

Thr Cys Gln Val Arg Lys Phe Tyr Pro Gln Ser Leu Gln Leu Thr Trp
            245                 250                 255

Ser Glu Asn Gly Asn Val Cys Gln Arg Glu Thr Ala Ser Thr Leu Thr
            260                 265                 270

Glu Asn Lys Asp Gly Thr Tyr Asn Trp Thr Ser Trp Phe Leu Val Asn
        275                 280                 285

Ile Ser Asp Gln Arg Asp Asp Val Val Leu Thr Cys Gln Val Lys His
    290                 295                 300

Asp Gly Gln Leu Ala Val Ser Lys Arg Leu Ala Leu Glu Val Thr Val
305                 310                 315                 320

His Gln Lys Asp Gln Ser Ser Asp Ala Thr Pro Gly Pro Ala Ser Ser
            325                 330                 335

Leu Thr Ala Leu Leu Leu Ile Ala Val Leu Leu Gly Pro Ile Tyr Val
            340                 345                 350

Pro Trp Lys Gln Lys Thr
        355

<210> SEQ ID NO 62
<211> LENGTH: 357
<212> TYPE: DNA
<213> ORGANISM: Artificial Sequence
<220> FEATURE:
<223> OTHER INFORMATION: polynucleotide encoding SiRP alpha variant

<400> SEQUENCE: 62
gaagaggagc tgcagatcat ccagcctgac aagtccgtgc tggtcgctgc tggtgaaact      60
gccactctgc gttgtacgat taccagcctg ttcccggtgg gtccaatcca gtggttccgt     120
ggtgctggtc cgggtcgtgt tctgatctac aaccagcgtc aaggtccgtt ccgcgtgta      180 actaccgtta gcgataccac gaagcgtaac aacatggact tttccatccg cattggcaat     240
attaccccgg ccgacgcggg cacctactat tgcatcaaat ttcgcaaagg ctccccggat     300
gatgtagaat taaatctggg cgcaggcacc gaactgtctg ttcgcgcaaa accgtaa       357

<210> SEQ ID NO 63
<211> LENGTH: 357
<212> TYPE: DNA
<213> ORGANISM: Artificial Sequence
<220> FEATURE:
<223> OTHER INFORMATION: human wild type SIRP alpha

<400> SEQUENCE: 63
gaggaggaat acaggtcat tcaaccagat aaatcggtct tagtagcagc ggagagaca        60 gctacattga gatgtacggc gacaagcctt attcccgtgg ggccgatcca atggtttcgc     120
ggggcaggcc ccggaagaga attgatttac aaccagaagg agggtcattt ccctcgcgtg     180
acgacggtca gcgacttaac taagcgtaat aacatggatt tttcaataag aataggcaat     240
ataactccgg ccgacgcagg gacgtactac tgtgttaaat ccggaagggg atctccggat     300
gatgtcgagt tcaaatctgg ggcgggtaca gaattgagcg ttcgggcaaa gccctaa       357

<210> SEQ ID NO 64
<211> LENGTH: 354
<212> TYPE: DNA

```
<213> ORGANISM: Artificial Sequence
<220> FEATURE:
<223> OTHER INFORMATION: wild type SIRP gamma

<400> SEQUENCE: 64
gaggaagaat tgcaaatgat ccagccggaa aaattattac tggttaccgt gggaaaaacg     60
gcgacccttc attgcacagt cacgtccctg ttgccggtag gtccagtttt gtggttccgg    120
ggggttggac cagggcgtga actgatctat aatcaaaagg aaggtcattt tccgcgcgtg    180
accacagtga gcgatttgac taaacggaac aatatggact tctcgatccg catttctagt    240
attacaccgg cggacgttgg cacttattat tgcgtcaagt ccgcaaagg aagtcctgag    300 aacgtagagt tcaagtccgg tcctggcact gagatggctt tgggtgctaa accc         354

<210> SEQ ID NO 65
<211> LENGTH: 354
<212> TYPE: DNA
<213> ORGANISM: Artificial Sequence
<220> FEATURE:
<223> OTHER INFORMATION: polynucleotide encoding SIRP gamma variant 1

<400> SEQUENCE: 65
gaagaggagc tgcagatcat ccagcctgac aagtccgtgc tggtcgctgc tggtgaaact    60
gccactctgc gttgtacgat taccagcctg ttcccggtgg gtccaatcca gtggttccgt   120
ggtgctggtc cggtcgtgt tctgatctac aaccagcgtc aaggtccgtt cccgcgtgta   180
actaccgtta gcgataccac gaagcgtaac aacatggact tttccatccg cattggcaat   240 attccccgg ccgacgcggg cacctactat tgcatcaaat ttcgcaaagg ctccccggat   300
gatgtagaat ttaaatctgg cgcaggcacc gaactgtctg ttcgcgcaaa accg         354

<210> SEQ ID NO 66
<211> LENGTH: 354
<212> TYPE: DNA
<213> ORGANISM: Artificial Sequence
<220> FEATURE:
<223> OTHER INFORMATION: polynucleotide encoding SIRP gamma variant 2

<400> SEQUENCE: 66
gaagaggaat tacaaatcat acaacctgaa aagctgttat tggtcaccgt aggcaaaacc    60
gctactctgc actgcactgt gacgtcccctt tttcctgttg gtcctgtctt atggtttcgt   120
ggagtcggtc cgggtcgggt tcttatctat aaccagcggc aaggaccatt cccacgggtt   180
accacggttt cggacacaac gaaacgcaat aacatggatt tttccattcg gatttcaagc   240
atcactccgg ccgacgttgg aacttattac tgcataaagt ttagaaaggg atctccggag   300
aacgtagaat ttaagtctgg tccaggtact gagatggccc ttggagcgaa gccg         354

<210> SEQ ID NO 67
<211> LENGTH: 24
<212> TYPE: DNA
<213> ORGANISM: Artificial Sequence
<220> FEATURE:
<223> OTHER INFORMATION: Forward primer

<400> SEQUENCE: 67
aaacatatgg aagaggagct gcag                                             24

<210> SEQ ID NO 68
<211> LENGTH: 27
<212> TYPE: DNA
<213> ORGANISM: Artificial Sequence
```

```
<220> FEATURE:
<223> OTHER INFORMATION: Reverse primer

<400> SEQUENCE: 68
aaaaagcttt caattcagat cctcttc                                              27
```